US012402975B2

(12) United States Patent
Naruse et al.

(10) Patent No.: US 12,402,975 B2
(45) Date of Patent: Sep. 2, 2025

(54) SURGICAL SUPPORT SYSTEM, SURGICAL SUPPORT METHOD, AND INFORMATION STORAGE MEDIUM

(71) Applicant: OLYMPUS CORPORATION, Tokyo (JP)

(72) Inventors: Masato Naruse, Hachioji (JP); Tomoko Gocho, Hachioji (JP); Tomoya Sakai, Hachioji (JP); Shunya Akimoto, Nishitokyo (JP); Kazumasa Kunugi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 669 days.

(21) Appl. No.: 17/840,880

(22) Filed: Jun. 15, 2022

(65) Prior Publication Data

US 2022/0401179 A1   Dec. 22, 2022

Related U.S. Application Data

(60) Provisional application No. 63/213,359, filed on Jun. 22, 2021.

(51) Int. Cl.
*G06F 3/04812* (2022.01)
*A61B 34/00* (2016.01)
*A61B 90/00* (2016.01)

(52) U.S. Cl.
CPC .............. *A61B 90/37* (2016.02); *A61B 34/25* (2016.02); *A61B 2034/256* (2016.02)

(58) Field of Classification Search
CPC ........... A61B 17/70; A61B 5/055; A61B 6/04; A61B 6/00; A61B 17/80; A61B 17/56;
(Continued)

(56) References Cited

U.S. PATENT DOCUMENTS

| 4,937,743 A | 6/1990 | Rassman et al. |
| 2008/0021738 A1 | 1/2008 | Komiya et al. |

(Continued)

FOREIGN PATENT DOCUMENTS

| JP | 2007-072894 A | 3/2007 |
| JP | 2007-122174 A | 5/2007 |

(Continued)

OTHER PUBLICATIONS

Japanese Office Action dated Jun. 30, 2023 received in 2022-097844.

(Continued)

*Primary Examiner* — Rayeez R Chowdhury
(74) *Attorney, Agent, or Firm* — Scully, Scott, Murphy & Presser, P.C.

(57) ABSTRACT

A surgical support system includes a processor that establishes communication connection with a terminal. The processor performs processing of displaying a display screen on a terminal to present the display screen to a member other than a surgeon among operation team members via the terminal. The display screen includes a live image region in which a live image of surgery conducted by the operation team members is displayed, and a supplementary region in which information regarding a supplementary operation selected by selection and input by a member via a terminal is displayed, the selection being made from a plurality of supplementary operations for management of the surge.

20 Claims, 29 Drawing Sheets

(58) Field of Classification Search
CPC ........... A61B 6/10; A61B 17/00; A61B 17/86; A61B 5/00
See application file for complete search history.

(56) References Cited

U.S. PATENT DOCUMENTS

| | | | |
|---|---|---|---|
| 2009/0125337 A1 | 5/2009 | Abri | |
| 2009/0317002 A1 | 12/2009 | Dein | |
| 2014/0267549 A1* | 9/2014 | Pinter | H04N 7/183 348/14.03 |
| 2014/0267658 A1 | 9/2014 | Speier et al. | |
| 2014/0379370 A1 | 12/2014 | Prigent | |
| 2015/0033128 A1* | 1/2015 | Curd | G16H 40/40 715/728 |
| 2015/0177952 A1 | 6/2015 | Meyer et al. | |
| 2015/0374259 A1 | 12/2015 | Garbey et al. | |
| 2016/0180281 A1 | 6/2016 | Cailliau et al. | |
| 2016/0188841 A1* | 6/2016 | Kudo | G16H 10/60 705/3 |
| 2016/0224195 A1 | 8/2016 | Okabe et al. | |
| 2017/0308823 A1 | 10/2017 | Bollapragada et al. | |
| 2018/0247128 A1* | 8/2018 | Alvi | H04L 67/12 |
| 2019/0332785 A1 | 10/2019 | AthuluruTIrumala | |
| 2020/0211720 A1* | 7/2020 | Goldberg | G16H 10/60 |
| 2020/0297422 A1 | 9/2020 | Gocho et al. | |
| 2020/0359893 A1* | 11/2020 | Rollins | G06F 3/04886 |
| 2021/0203889 A1* | 7/2021 | Fung | H04N 7/183 |
| 2022/0037038 A1 | 2/2022 | Robbins et al. | |
| 2022/0104910 A1* | 4/2022 | Shelton, IV | G06F 3/012 |
| 2022/0406446 A1 | 12/2022 | Naruse et al. | |
| 2022/0406447 A1 | 12/2022 | Naruse et al. | |
| 2022/0406448 A1 | 12/2022 | Naruse et al. | |
| 2023/0057961 A1* | 2/2023 | Roh | G16H 50/50 |

FOREIGN PATENT DOCUMENTS

| | | |
|---|---|---|
| JP | 2007-249251 A | 9/2007 |
| JP | 2013-081558 A | 5/2013 |
| JP | 2015-149063 A | 8/2015 |
| WO | 2010/119892 A1 | 10/2010 |
| WO | 2013/082289 A1 | 6/2013 |
| WO | 2019/116593 A1 | 6/2019 |

OTHER PUBLICATIONS

Y. Liu, et al., "Real-Time Streaming of Surgery Performance and Intraoperative Imaging Data in the Hybrid Operating Room: Development and Usability Study", JMIR Med Inform. Apr. 22, 2020;8(4):e18094. doi: 10.2196/18094. PMID: 32209528; PMCID: PMC7316181 (Year: 2020).

US Office Action dated Sep. 9, 2024 received in U.S. Appl. No. 17/840,894.

Extended European Search Report dated Nov. 18, 2022 received in 22180038.6.

US Office Action issued Apr. 24, 2024 received in U.S. Appl. No. 17/840,842.

Japanese Office Action dated Jun. 13, 2023 received in 2022-097843.

US Office Action dated Mar. 17, 2025 received in U.S. Appl. No. 17/840,867.

Combs, C. Andrew et al., "Society for Maternal-Fetal Medicine Special Statement: Surgical safety checklists for ceasarean delivery", American journal of Obstetrics & Genecology, vol. 225, Issue 5, B43-49 (Year:2021).

* cited by examiner

FIG. 9

| NAME OF CHECK LIST | DISPLAY CONTENTS |
|---|---|
| ROOM-ENTRY CHECK LIST | MEDICAL RECORD (PATIENT IDENTIFICATION INFORMATION) |
| | ID CARD (PATIENT IDENTIFICATION INFORMATION) |
| | WRISTBAND (PATIENT IDENTIFICATION INFORMATION) |
| | CONSENT FORM FOR SURGERY (PRIOR CONSENT INFORMATION) |
| | CONSENT FORM FOR ANESTHESIA (PRIOR CONSENT INFORMATION) |
| | TYPE AND NUMBER OF ANTIBIOTICS (EQUIPMENT/MEDICINE PREPARATION INFORMATION) |
| | MARKING (MARKING INFORMATION) |
| | BLOOD TRANSFUSION ORDER TABLE (EQUIPMENT/MEDICINE PREPARATION INFORMATION) |
| | ITEMS REQUIRED FOR EACH OPERATIVE METHOD (EQUIPMENT/MEDICINE PREPARATION INFORMATION) |

FIG. 10

| NAME OF CHECK LIST | DISPLAY CONTENTS |
|---|---|
| SIGN-IN | SURGICAL SITE MARKED? (MARKING INFORMATION) |
| | ANESTHETIC MACHINE AND MEDICINE CHECK COMPLETED? (EQUIPMENT/MEDICINE CHECK INFORMATION) |
| | PULSE OXIMETER ATTACHED TO PATIENT AND IN OPERATION? (EQUIPMENT/MEDICINE CHECK INFORMATION) |
| | PATIENT HAVE KNOWN ALLERGY? (PATIENT'S RISK INFORMATION) |
| | PATIENT HAS A RISK OF DIFFICULTY IN AIRWAY CONTROL OR ACCIDENTAL INGESTION? (PATIENT'S RISK INFORMATION) |
| | HEMORRHAGE RISK OF PATIENT IS 500 ML (7 ML/KG FOR CHILDREN) OR MORE? (PATIENT'S RISK INFORMATION) |

FIG. 11

| NAME OF CHECK LIST | DISPLAY CONTENTS |
|---|---|
| TIME-OUT | SCHEDULED SURGERY TIME? (SCHEDULE INFORMATION) |
| | ESTIMATED HEMORRHAGE AMOUNT? (ESTIMATED SURGERY PROGRESS INFORMATION) |
| | PROPHYLACTIC ANTIMICROBIAL ADMINISTRATION WAS DONE WITHIN LATEST 60 MINUTES? (MEDICINE PREPARATION INFORMATION) |
| | STERILIZATION OF INSTRUMENT WAS CONFIRMED? (EQUIPMENT PREPARATION INFORMATION) |
| | ANY CONCERN ABOUT PROCEDURE AND PATIENT? (ESTIMATED SURGERY PROGRESS INFORMATION) |

FIG. 12

| NAME OF CHECK LIST | DISPLAY CONTENTS |
|---|---|
| SIGN-OUT | NAME OF PATIENT, NAME OF DISEASE, NAME OF OPERATIVE METHOD?(PATIENT/SURGERY IDENTIFICATION INFORMATION) |
| | NUMBERS OF EQUIPMENT, GAUZES (SPONGES) AND NEEDLES ARE CORRECT? (INFORMATION OF NUMBER OF EQUIPMENT) |
| | PULSE OXIMETER ATTACHED TO PATIENT AND IN OPERATION? (EQUIPMENT OPERATION INFORMATION) |
| | DISPLAY OF SPECIMEN (SPECIMEN INFORMATION) |
| | ANY EQUIPMENT ISSUES TO HANDLE? (EQUIPMENT OPERATION INFORMATION) |
| | ANY KEY CONCERNS IN POST-SURGERY RECOVERY OR MANAGEMENT OF PATIENT? (ESTIMATED POST-SURGERY PROGRESS INFORMATION) |

FIG. 13

| NAME OF CHECK LIST | CIRCULATING NURSE (FIRST TERMINAL) | SCRUB NURSE (SECOND TERMINAL) | ANESTHESIOLOGIST (THIRD TERMINAL) | SURGEON (MONITOR) |
|---|---|---|---|---|
| ROOM-ENTRY CHECK LIST (FOURTH CHECK LIST) | ○ | × | × | × |
| SIGN-IN (FIRST CHECK LIST) | ○ | × | ○ | × |
| TIME-OUT (SECOND CHECK LIST) | ○ | ○ | ○ | ○ |
| SIGN-OUT (THIRD CHECK LIST) | ○ | ○ | ○ | ○ |

FIG. 17
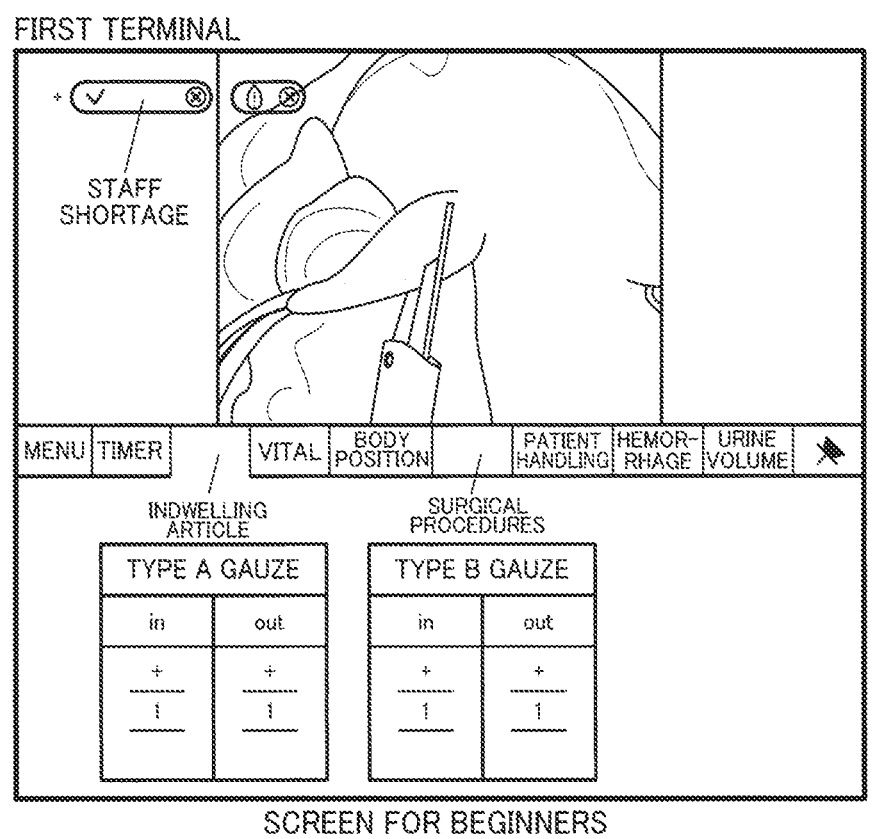
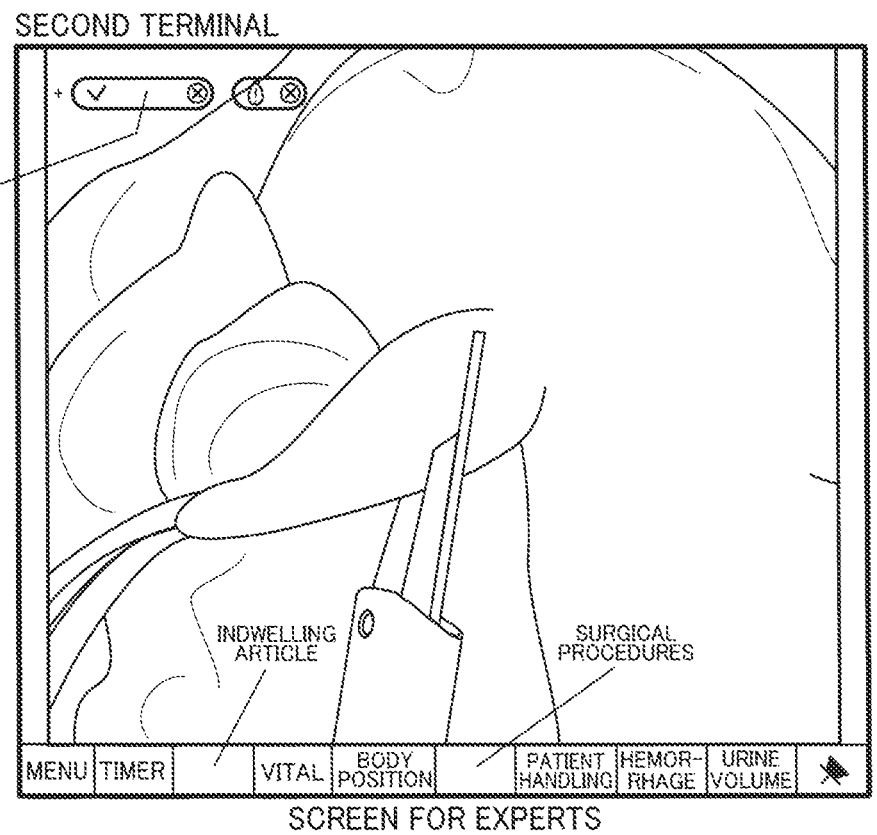

FIG. 18

SURGICAL SUPPORT SYSTEM, SURGICAL SUPPORT METHOD, AND INFORMATION STORAGE MEDIUM

CROSS REFERENCE TO RELATED APPLICATION

This application is based upon and claims the benefit of priority to U.S. Provisional Patent Application No. 63/213,359 filed on Jun. 22, 2021, the entire contents of which are incorporated herein by reference.

BACKGROUND

International Publication No. WO2019/116593 discloses a surgery support system. The processor of the surgery support system generates real-time data including real-time position information with regard to a characteristic part in a body cavity based on at least preoperative data and an endoscopic image, and, based on the real-time data, generates an image to be superimposed on the endoscopic image when displayed.

Further, Japanese Unexamined Patent Application Publication No. JP2007-249251 discloses a clinical communication device. The clinical communication device includes electronic medical record information extraction means for extracting electronic medical record information from electronic medical record database, clinical communicator information extraction means for extracting clinical communication information from clinical communicator database, information update means for updating the electronic medical record information and/or the clinical communication information in accordance with inputs, and display control means for displaying the electronic medical record information and the clinical communication information in linkage with each other. The electronic medical record information includes at least a clinical path, medical record information of a patient, and a clinical course of a patient. The clinical communication information includes at least patient's event information, medical service worker's event information, and messages from medical service workers.

SUMMARY

According to one aspect of the invention, there is provided a surgical support system, comprising:
a processor configured to establish communication connection with a terminal, and perform processing of displaying a display screen on the terminal to present the display screen via the terminal to a member other than a surgeon among operation team members,
wherein the display screen includes
a live image region in which a live image of surgery conducted by the operation team members is displayed, and
a supplementary region in which information regarding a supplementary operation selected by selection and input by the member via the terminal is displayed, the selection being made from a plurality of supplementary operations for management of the surgery.

According to another aspect of the invention, there is provided a surgical support method comprising:
performing processing of displaying a display screen having a live image region and a supplementary region on a terminal to present the display screen via the terminal to a member other than a surgeon among operation team members;
displaying a live image of surgery conducted by the operation team members in the live image region of the display screen; and
displaying information regarding a supplementary operation selected by selection and input by the member via the terminal, the selection being made from a plurality of supplementary operations for management of the surgery.

According to another aspect of the invention, there is provided a non-transitory information storage medium storing a program for causing a computer to execute
performing processing of displaying a display screen having a live image region and a supplementary region on a terminal to present the display screen via the terminal to a member other than a surgeon among operation team members;
displaying a live image of surgery conducted by the operation team members in the live image region of the display screen; and
displaying information regarding a supplementary operation selected by selection and input by the member via the terminal, the selection being made from a plurality of supplementary operations for management of the surgery.

BRIEF DESCRIPTION OF DRAWINGS

FIG. 9 is an example of display contents of a room-entry check list.
FIG. 10 is an example of display contents of a sign-in check list.
FIG. 11 is an example of display contents of a time-out check list.
FIG. 12 is an example of display contents of a sign-out check list.
FIG. 13 is an example of members in charge of each check list.
FIG. 17 is an example of display mode according to skill or proficiency level.
FIG. 18 is an example of alert sign for indwelling article count.

DESCRIPTION OF EXEMPLARY EMBODIMENTS

Figure 1:
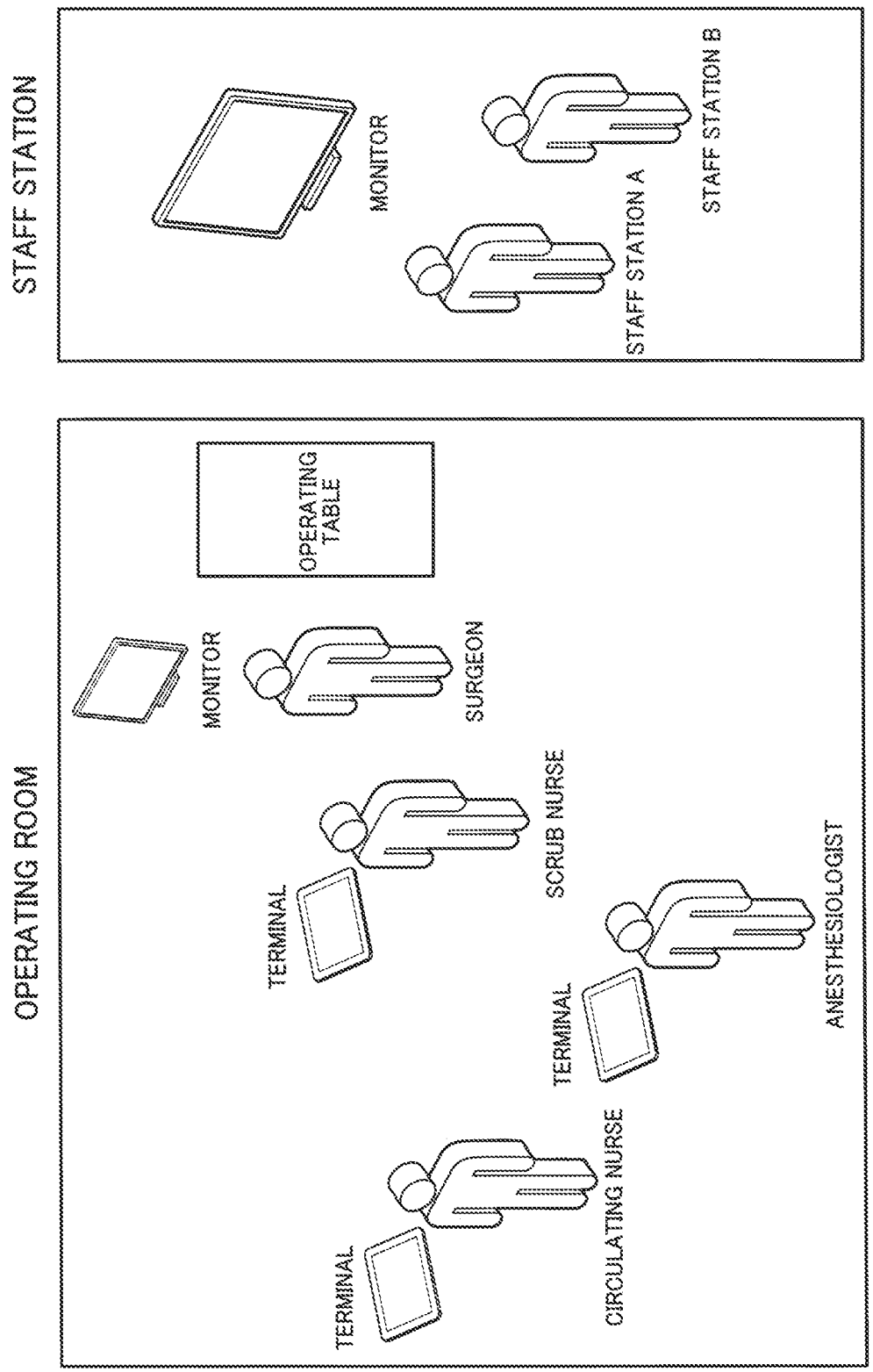
FIG. 1 is a diagram illustrating staff involved in surgery and a surgical support system of the present embodiment.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Configuration Example

FIG. 1 is a diagram for explaining staff involved in surgery and a surgical support system of the present embodiment. Although only one operating room is illustrated in FIG. 1, a plurality of operating rooms may be provided.

The staff station is a room separated from the operating room, and if there are a plurality of operating rooms, the staff station is provided in common to the plurality of operating rooms. The staff station has staff members A and B who perform clerical surgery management. At least one staff member is necessary. The surgery management is, for example, management of surgery schedule, management of surgery resources, arrangement of staff, instruments, or blood transfusion packs during surgery, and the like. The surgery schedule displayed on a monitor may be viewed and operated by the staff members A and B. The number of monitors is not limited to one. For example, the surgery schedule may be displayed on a terminal of each staff member.

When surgery is performed in an operating room, a surgeon(s), a circulating nurse(s), a scrub nurse(s), and an anesthesiologist(s) are distributed in the operating room. They are medical service workers, and will be hereinafter referred to as operation team members. The operation team members are not always required to stay in the operating room during the surgery flow. For example, when a sign-in check list is checked, the surgeon may be getting ready for the surgery outside the operating room, and the circulating nurse may exit and reenter the operating room to replenish staff, instruments, blood transfusion packs, and the like. The sign-in is an action of checking a check list that is checked before induction of anesthesia.

A surgeon is a doctor responsible for performing an operation in surgery. A scrub nurse prepares instruments necessary for the surgery, and, for example, passes instruments such as scalpels to the surgeon during the surgery. During the surgery, the surgeon and the scrub nurse act in a clean area near the operating table. An anesthesiologist is a doctor who administers anesthesia to a patient. A circulating nurse provides support for smooth progress of surgery. The operation team members are not limited to a surgeon as a physician in charge of operation, a scrub nurse, an anesthesiologist, and a circulating nurse, and may include other members. For example, the operation team members may include, as a surgeon, one or both of an assistant or a scopist. Although the surgeon in the following description is mainly assumed to be a doctor in charge of an operation, the surgeon is not limited to the doctor in charge of the operation, as described above.

The monitor viewed by the surgeon displays a surgery image showing the surgical field or a surgical support image obtained by adding support information to the surgery image. There may be two or more monitors viewed by the surgeon. The circulating nurse, the scrub nurse, and the anesthesiologist use the terminals to perform monitoring, assist, support, and the like of the surgery. Each terminal displays a surgery image showing the surgical field, a surgical support image obtained by adding support information to the surgery image, a check list for each stage of surgery, supplementary information for assisting surgery, various alerts, and the like. Although information is shared among all terminals, each member can independently operate the terminal, and each member can independently select what is to be displayed on his/her terminal. However, the screen may be automatically switched to a check list or the like according to the surgery flow.

Figure 2:
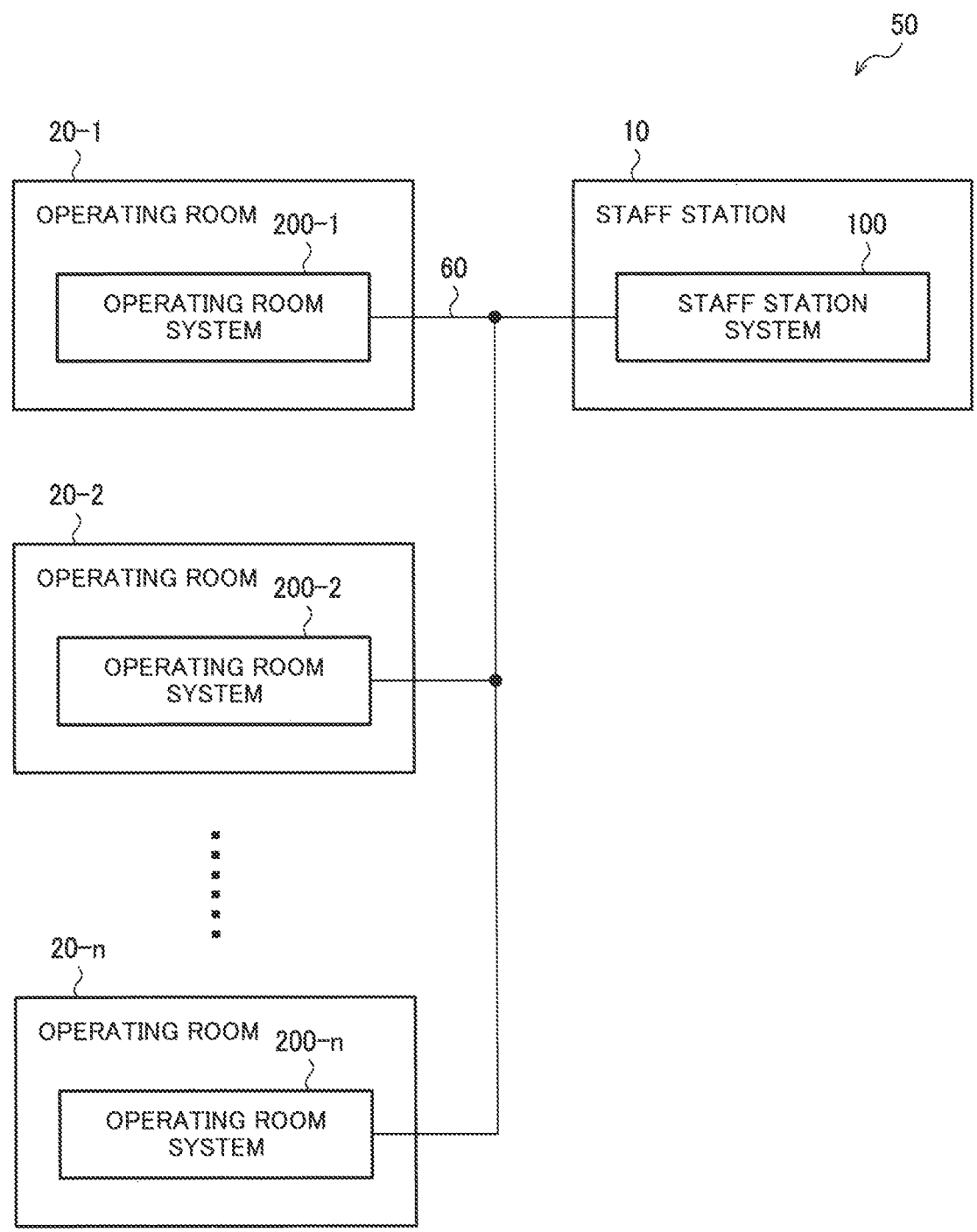
FIG. 2 is a configuration example of a surgical support system of the present embodiment.

FIG. 2 is a configuration example of a surgical support system 50 of the present embodiment. The surgical support system 50 includes a staff station system 100 provided in the staff station 10 and operating room systems 200-1 to 200-n provided in operating rooms 20-1 to 20-n, where n is an integer equal to or greater than 1. The staff station system 100 and the operating room systems 200-1 to 200-n are connected by wired communication 60, such as a wired LAN. However, the staff station system 100 and the operating room systems 200-1 to 200-n may be connected by wireless communication.

Each of the staff station system 100 and the operating room systems 200-1 to 200-n or the entire surgical support system 50 may be configured by a cloud system. In this case, for example, a cloud part of the surgical support system 50 may exist outside the staff station 10, and terminals connected to the cloud system may exist inside the staff station 10. The same applies to the operating room support system.

Figure 3:
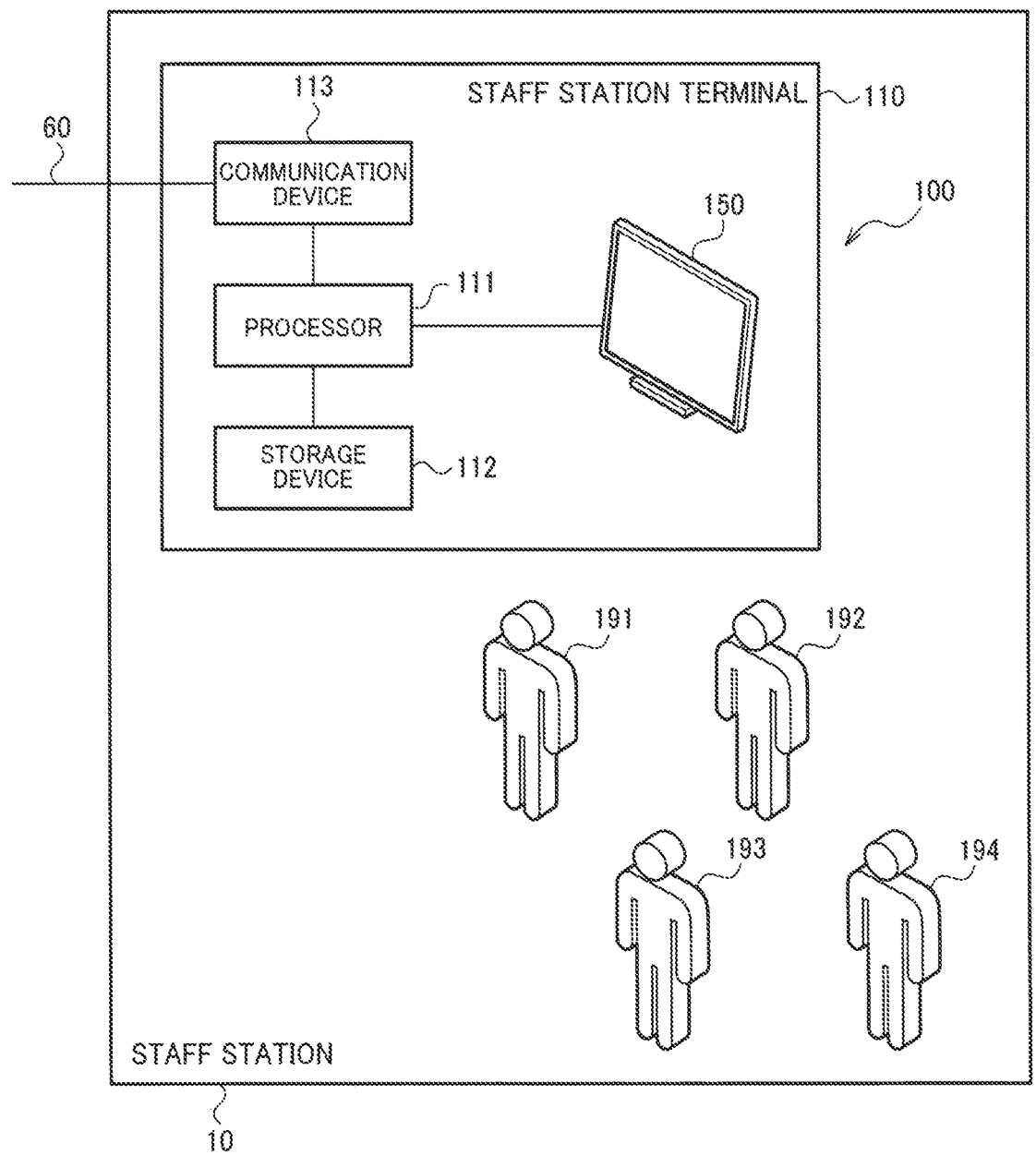
FIG. 3 is a detailed configuration example of a system for staff station.

FIG. 3 is a detailed configuration example of staff station system 100. The staff station system 100 includes a staff station terminal 110. The staff station terminal 110 includes a processor 111, a storage device 112, a communication device 113, and a monitor 150.

The processor 111 executes various processes related to surgery management. The processor 111 performs, for example, processing of displaying a surgery schedule screen on the monitor 150, processing of changing the surgery schedule according to operation inputs from staff members 191 to 194, processing of exchanging information with the operating room systems 200-1 to 200-n via the communication device 113, processing of displaying an alert or the like on the monitor 150 based on the content of the communication, and the like. The processor 111 is also referred to as a processing section, a processing device, or the like. The processor 111 includes hardware, and may be, for example, a central processing unit (CPU), a microcomputer, a graphics processing unit (GPU), or the like, or may be an application specific integrated circuit (ASIC), a field programmable gate array (FPGA), or the like.

The storage device 112 is a semiconductor memory, a hard disk drive, an optical drive, or the like. The semiconductor memory is a volatile memory such as a random access memory (RAM) or a nonvolatile memory such as an electrically erasable programmable read only memory (EEPROM). The storage device 112 stores a program in which the processes to be executed by the staff station terminal 110 are described. The processor 111 reads out a program from the storage device 112 and executes the program. In addition, the storage device 112 stores various types of data necessary for surgery management or functions as a working memory of the processor 111.

The communication device 113 performs communication with the operating room systems 200-1 to 200-n according to the communication standard of the wired communication 60.

The monitor 150 is, for example, a liquid crystal display device, an electro-luminescence (EL) display device, or the like. The monitor 150 includes a touch panel, and the processor 111 accepts operation inputs from the staff members 191 to 194 via the touch panel. However, the operation inputs are not limited to those made to the touch panel, and may be performed by a pointing device such as a mouse, for example.

The hardware configuration of the staff station terminal 110 is not limited to that shown in FIG. 3. For example, the staff station terminal 110 may include a plurality of monitors, or may be configured by an information processing device and a plurality of mobile terminals with individual monitors.

Figure 4:
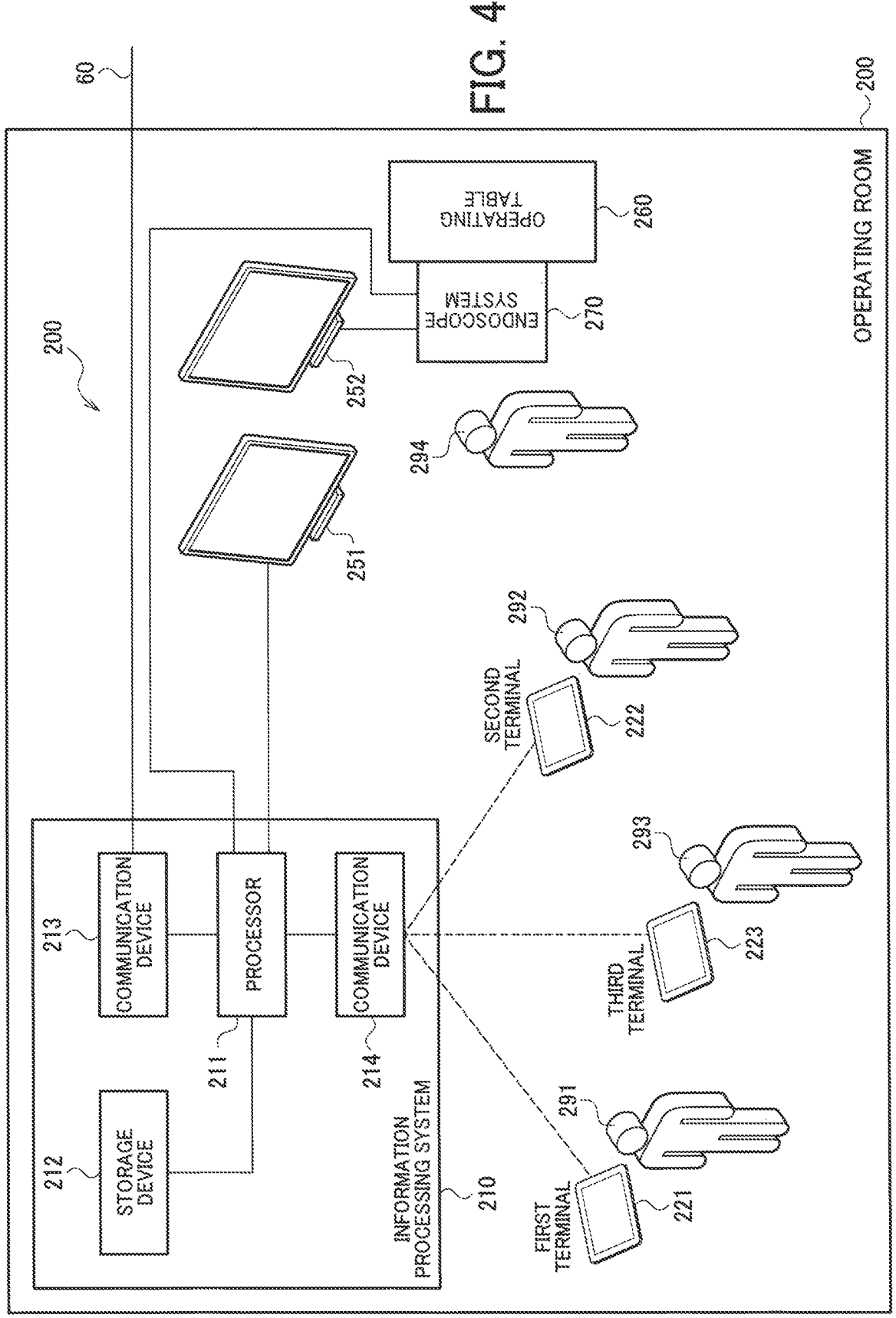
FIG. 4 is a detailed configuration example of a system for operating room.

FIG. 4 is a detailed configuration example of an operating room system 200. The operating room system 200 corresponds to each of the operating room systems 200-1 to 200-n in FIG. 2. The operating room system includes an information processing system 210, a first terminal 221, a second terminal 222, a third terminal 223, a support monitor 251, an endoscope monitor 252, and an endoscope system 270. Although an example of surgery using the endoscope system 270 will be described below, the operating room support system according to the present embodiment may be used for a surgery that is performed without the endoscope system 270. In this case, for example, a camera that captures an image of the surgical field and a monitor that displays the camera image may be provided.

The endoscope system 270, the support monitor 251, and the endoscope monitor 252 are disposed near the operating table 260 for use or observation by a surgeon 294. The endoscope system 270 includes an endoscope, an image processing device for processing images captured by the endoscope, and the like. The image processing device of the endoscope system 270 displays on the endoscope monitor 252 an endoscopic image captured by the endoscope as a surgery image.

The information processing system 210 includes a processor 211, a storage device 212, a communication device 213, and a communication device 214. The information processing system 210 may be configured by one or a plurality of information processing devices, or may be implemented by a cloud system. For example, the information processing system 210 may be configured by a data server that acquires and accumulates accumulated data such as electronic medical records, and an information processing device that performs surgical support for the operation team members or performs cooperation with the staff station terminal 110.

The first member 291, the second member 292, and the third member 293 are operation team members other than the surgeon 294. In particular, the first member 291 is a circulating nurse, the second member 292 is a scrub nurse, and the third member 293 is an anesthesiologist. However, the roles of these members are not limited to those described above, and the first member 291 may be a member with a first role other than the surgeon, the second member 292 may be a member with a second role other than the surgeon and the first role, and the third member 293 may be a member with a third role other than the surgeon, the first role, and the second role.

Among a plurality of terminals included in the operating room system, a terminal allocated to the first member 291 is a first terminal 221, a terminal allocated to the second member 292 is a second terminal 222, and a terminal allocated to the third member 293 is a third terminal 223. Any arbitrary one of the plurality of terminals may be allocated to each member. For example, it is possible to allocate a terminal to each member using ID authentication or the like.

One or more members may be assigned to each role, and two or more members may be assigned to the same role. For example, the operation team members may further include a fourth member who is a circulating nurse. In this case, it is possible to allocate individual terminals to the first and the fourth members, who are the circulating nurses, or allocate a single common terminal to them. In either case, the first terminal 221 is allocated to the first member 291, who is a circulating nurse.

The processor 211 executes various processes related to surgical support. The processor 211 performs, for example, processing of displaying various images or various types of information on the terminals via the communication device 214, processing of displaying various images or various types of information on the support monitor 251, processing of updating information such as a check list in response to an operation input from each member, processing of exchanging information with the staff station terminal 110 via the communication device 213, processing of displaying information on the terminals or the support monitor 251 based on the content of the communication, and the like. The processor 211 is also referred to as a processing section, a processing device, or the like. The processor 111 includes hardware, and may be, for example, a CPU, a microcomputer, a GPU, or the like, or may be an ASIC, an FPGA, or the like.

The storage device 212 is a semiconductor memory, a hard disk drive, an optical drive, or the like. The semiconductor memory is a volatile memory such as a RAM or a nonvolatile memory such as an EEPROM. The storage device 212 stores a program in which the processes to be executed by the information processing system 210 are described. The processor 211 reads out a program from the storage device 212 and executes the program. Further, the storage device 212 stores various types of data necessary for surgical support, accumulates accumulated data such as electronic medical records, or functions as a working memory of the processor 211.

The communication device 213 performs communication with the staff station terminal 110 via the wired communication 60.

The support monitor 251 and the endoscope monitor 252 is, for example, a liquid crystal display device, an EL display device, or the like. The support monitor 251 and the endoscope monitor 252 can be, but not limited to, a monitor without a touch panel. The support monitor 251 and the endoscope monitor 252 may not be two monitors; instead, they may be provided by dividing a display region of a single monitor, for example.

The communication device 214 performs communication with the first terminal 221, the second terminal 222, and the third terminal 223 through wireless communication, such as a wireless LAN. The communication device 214 may communicate with the first terminal 221, the second terminal 222, and the third terminal 223 through wired communication, such as a wired LAN.

Figure 5:
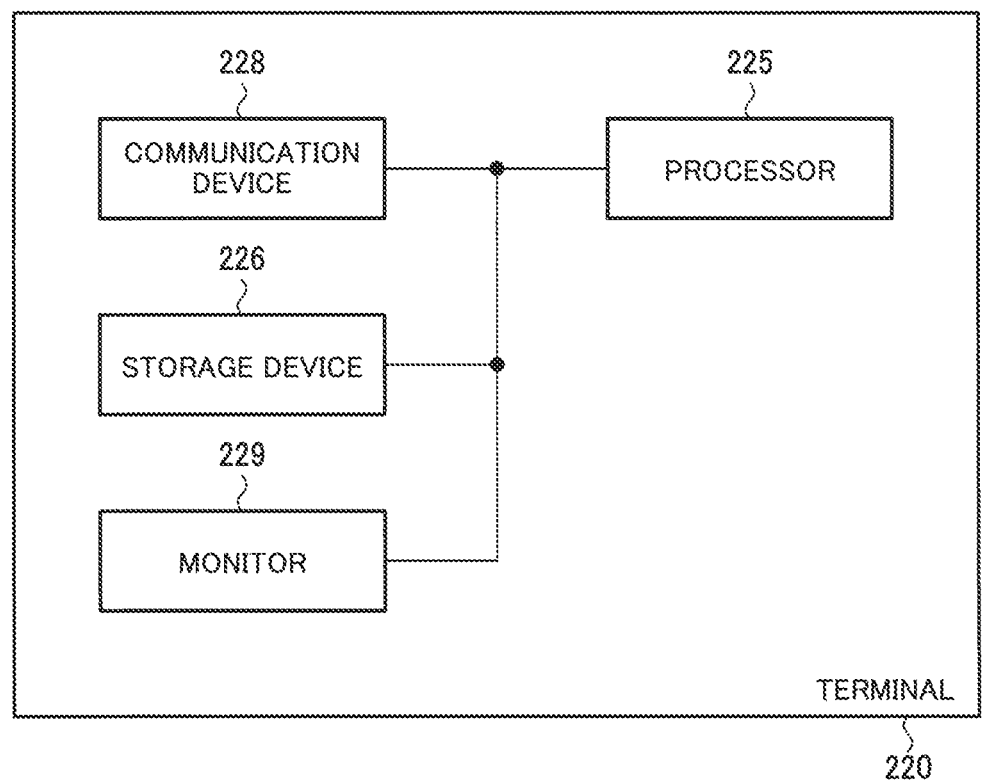
FIG. 5 is a detailed configuration example of a terminal.

The first terminal 221, the second terminal 222, and the third terminal 223 may be, but not limited to, mobile terminals, such as tablet-type terminals. FIG. 5 is a detailed configuration example of a terminal 220. The terminal 220 corresponds to each of the first terminal 221, the second terminal 222, and the third terminal 223. The terminal 220 includes a processor 225, a storage device 226, a communication device 228, and a monitor 229.

The communication device 228 performs communication with the information processing system 210 by wireless communication. The storage device 226 stores a program in which the processes to be executed by the terminal 220 are described. The processor 225 reads out a program from the storage device 226 and executes the program. The storage device 212 also functions as a working memory of the processor 225. The processor 225 displays various images or various types of information transmitted from the information processing system 210 on the monitor 229. The monitor 229 includes a touch panel, and the processor 225 accepts an operation input via the touch panel from a member having the terminal 220.

Figure 6:
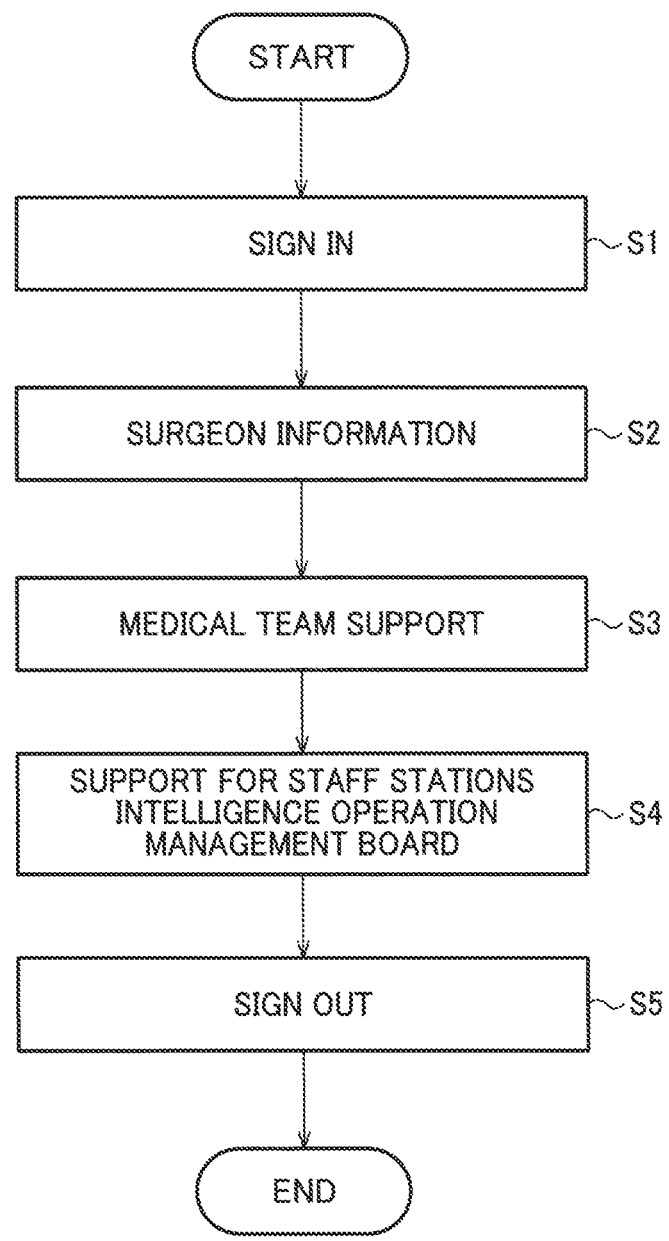
FIG. 6 shows a flow of surgical support using a surgical support system.

FIG. 6 shows a flow of surgical support using the surgical support system 50. Although a flow relating to a surgery is shown below, the surgical support system 50 can provide a function such as management of surgery schedule to the staff in the staff station 10 when no surgery is performed.

In step S1, the operating room system 200 displays a sign-in check list on the first terminal 221 of the circulating nurse and the third terminal 223 of the anesthesiologist. The circulating nurse and the anesthesiologist check the sign-in check list. Between step S1 and step S5, steps S2 to S4 may be performed in random order or in parallel.

In step S2, the operating room system 200 provides support information for supporting the surgery to the surgeon. For example, the operating room system 200 performs an image recognition process on a live image from an endoscope to detect a hemorrhage area or a landmark from the live image, or performs distance measurement in the live image. The operating room system 200 superimposes the recognition result on the live image as support information and displays the resulting image on the support monitor 251. Various algorithms can be used for the image recognition process, and examples include an image recognition process using machine learning. In this case, the storage device 212 stores a trained model that has been trained to output a recognition result, such as a hemorrhage area, from an input endoscopic image. The processor 211 assumes a hemorrhage area or the like from the endoscopic image by processing based on the trained model, superimposes the assumption result on the live image, and displays the resulting image on the support monitor 251.

In step S3, the operating room system 200 supports operation team members other than the surgeon. For example, the operating room system 200 provides functions such as a timer, a gauze counter, vital notification, body position notification, surgical procedure notification, risk notification for each patient, hemorrhage notification, or urine volume notification to each member via the first terminal 221, the second terminal 222, and the third terminal 223.

In step S4, the staff station system 100 provides support to the staff in the staff station 10. For example, the staff station system 100 provides a scheduler function to the staff. Specifically, the staff station system 100 displays on the monitor 150 a surgery schedule, an instrument list, a staff list, or the like to allow the staff to manage the surgery schedule using a touch panel or the like. Alternatively, the staff station system 100 supports the staff in conjunction with the operating room system 200. Specifically, the staff station system 100 displays surgery progress information received from the operating room system 200, alert information, a real-time surgery video showing the inside of the operating room, or the like on the schedule screen of the monitor 150. Alternatively, the staff station system 100 stores the surgery progress information received from the operating room system 200, the alert information, the live image from the endoscope, the real-time surgery video showing the inside of the operating room, and the like in association with each other, and displays history information based on the record on the monitor 150.

In step S5, the operating room system 200 displays a sign-out check list on the first terminal 221 of the circulating nurse, the second terminal 222 of the scrub nurse, the third terminal 223 of the anesthesiologist, and the support monitor 251 of the surgeon. The circulating nurse, the scrub nurse, the anesthesiologist, and the surgeon check the sign-out check list.

Figure 7:
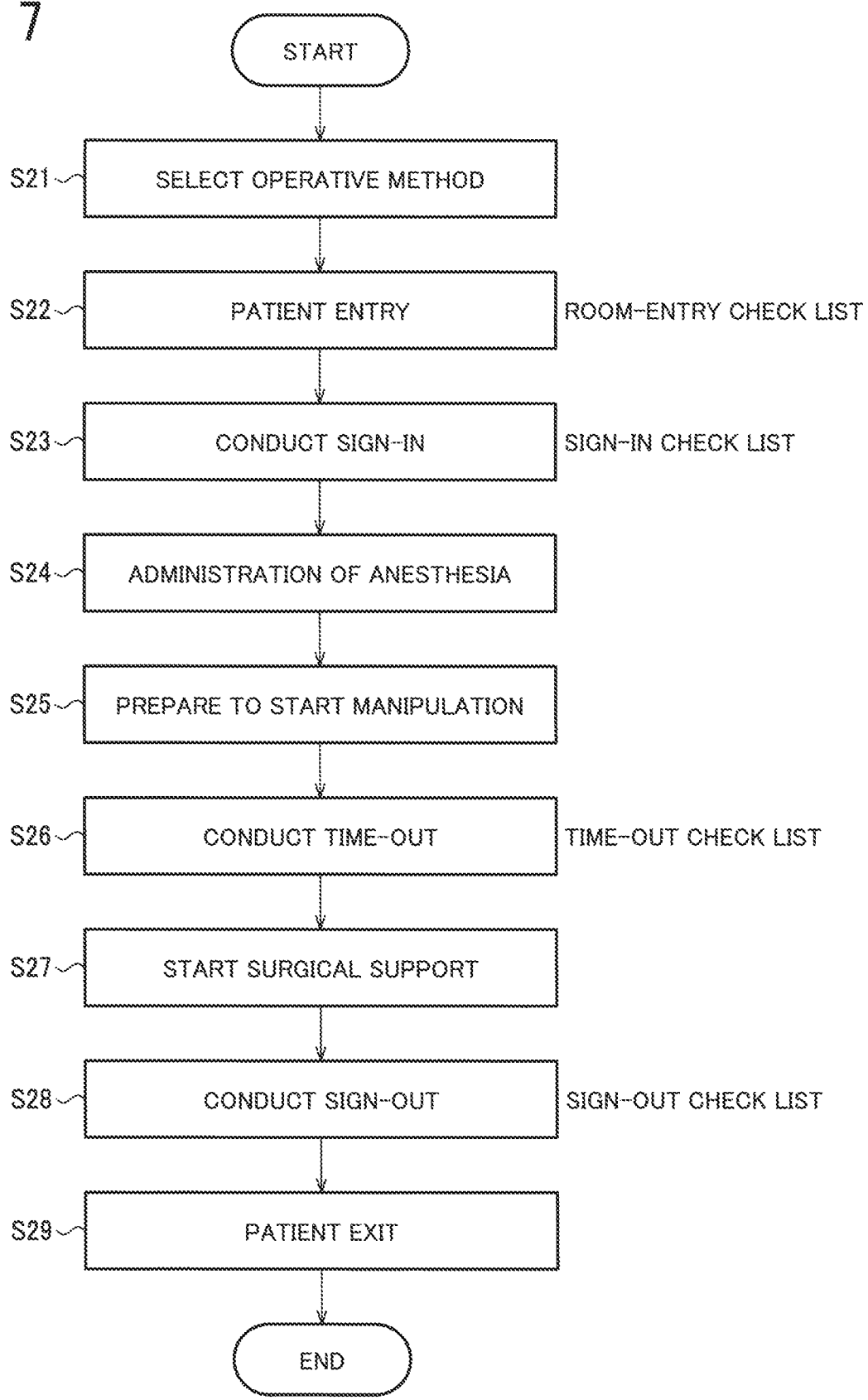
FIG. 7 shows a flow of checking timing of a check list.

FIG. 7 shows a flow of checking timing of a check list. In step S21, the operation team members select an operative method.

In step S22, an operation team member brings a patient in the operating room. At this time, the operating room system 200 displays a room-entry check list on the first terminal 221 of the circulating nurse, and the circulating nurse checks the room-entry check list.

In step S23, an operation team member performs sign-in. The sign-in is an action of checking a check list that is checked before induction of anesthesia. At this time, the operating room system 200 displays a sign-in check list on the first terminal 221 of the circulating nurse and the third terminal 223 of the anesthesiologist. The circulating nurse and the anesthesiologist check the sign-in check list.

In step S24, the anesthesiologist administers anesthesia to the patient. In step S25, the surgeon gets ready for the manipulation. In step S26, an operation team member performs time-out. The time-out is an action of checking a pre-skin-incision check list. At this time, the operating room system 200 displays a time-out check list on the first terminal 221 of the circulating nurse, the second terminal 222 of the scrub nurse, and the third terminal 223 of the anesthesiologist, and the support monitor 251 of the surgeon. The circulating nurse, the scrub nurse, the anesthesiologist, and the surgeon check the time-out check list.

In step S27, the surgical support system 50 starts surgical support using an image recognition process. In step S28, after the surgical support of the surgical support system 50 is completed, an operation team member performs sign-out. The sign-out is an action of checking a pre-room-exit check list. At this time, the operating room system 200 displays a sign-out check list on the first terminal 221 of the circulating nurse, the second terminal 222 of the scrub nurse, the third terminal 223 of the anesthesiologist, and the support monitor 251 of the surgeon. The circulating nurse, the scrub nurse, the anesthesiologist, and the surgeon check the sign-out check list.

In step S29, an operation team member takes the patient out of the operating room.

Figure 8:
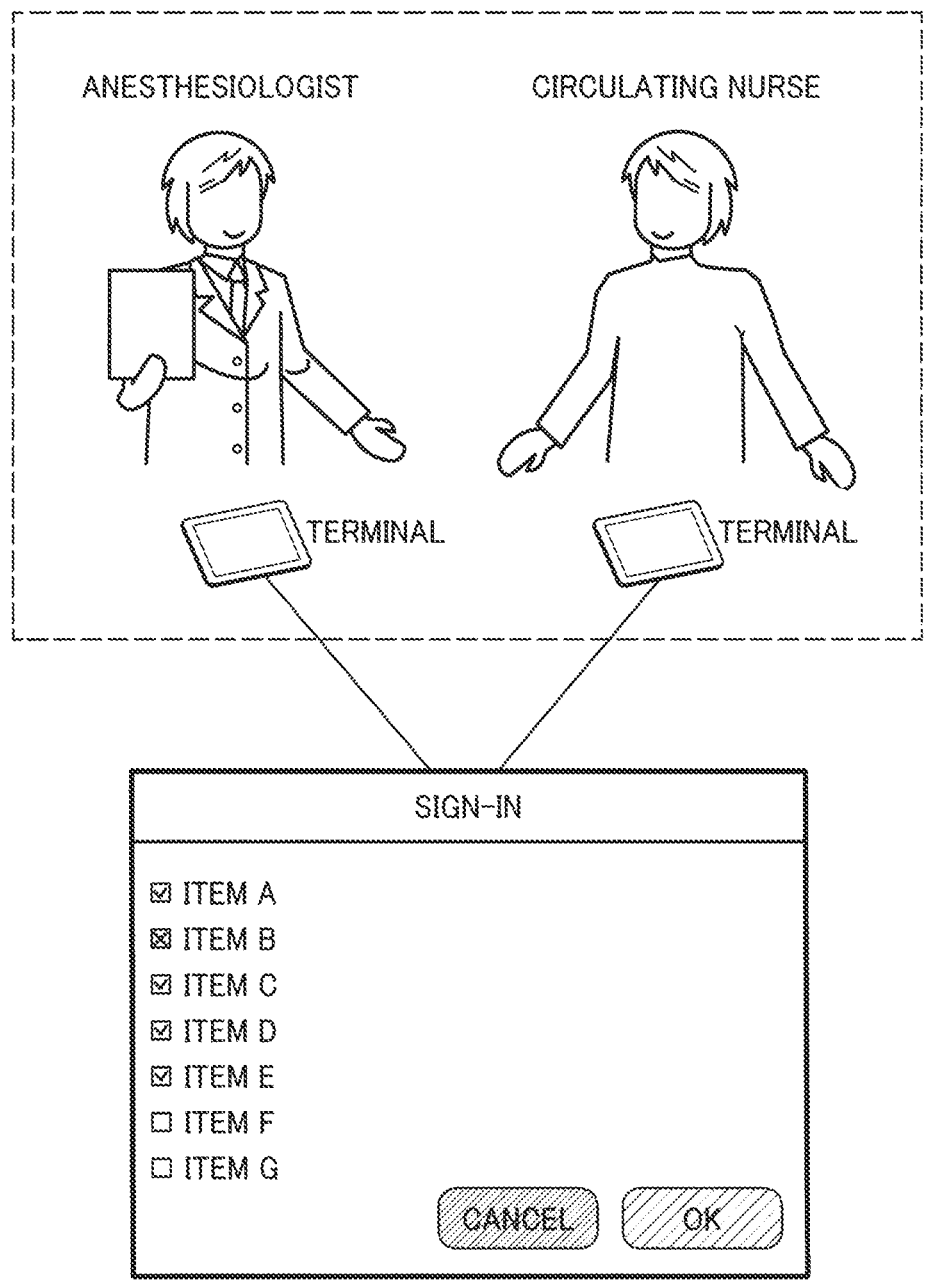
FIG. 8 is an explanatory view of display and operation of a check list.

FIG. 8 is an explanatory view of display and operation of a check list. As an example, the "sign-in" is described below.

A plurality of items and check boxes for the individual items are displayed in the sign-in check list. FIG. 8 shows an example in which items A to G are displayed; however, the number of items is not limited to this example. The members can change the check status of each item by tapping a corresponding check box on the touch panel. In the sign-in check list, a cancel button, a OK button, and the like are also displayed. The members can cancel or complete the checking action by tapping the cancel button or the OK button on the touch panel. The details of the check list operation is described later.

The same sign-in check list is displayed on both of the first terminal 221 of the circulating nurse and the third terminal 223 of the anesthesiologist, and the check status thereof is shared between the first and third terminals 221 and 223. Specifically, the storage device 212 of the operating room system 200 stores check status data indicating check statuses of the check list. The processor 211 updates the shared check status data in the storage device 212 when the circulating nurse inputs information to the check list via the first terminal 221 or when the anesthesiologist inputs information to the check list via the third terminal 223. The processor 211 performs processing of displaying the check list on the first terminal 221 and the third terminal 223 based on the updated check status data. Accordingly, the check statuses in the check list are shared between the first terminal 221 and the third terminal 223.

The "process of displaying a check list on a terminal by the processor" may be any process of enabling the processor to transmit check list-related data to a terminal, thus allowing the terminal to display the check list based on the data. For example, the processor may generate a display image of the check list based on the check status data and transmit the display image to the terminal, thus allowing the terminal to display the display image of the check list on the monitor of the terminal. Alternatively, the processor may transmit the check status data to the terminal, thus allowing the terminal to generate the display image of the check list based on the check status data and display the image on the monitor of the terminal. Although the "process of displaying" was described above using the check list as an example, the "process of displaying" means the same also when information other than the check list is displayed on the terminal.

FIG. 9 is an example of display contents of a room-entry check list. One field of the display contents indicates one check item.

The room-entry check list includes, as the check items, "medical record", "ID card", and "wristband". These items are referred to as patient identification information. The room-entry check list also includes, as the check items, "consent form for surgery" and "consent form for anesthesia". These items are referred to as prior consent information. In addition, the room-entry check list also includes, as the check items, "type and number of antibiotics", "blood transfusion order table", and "items required for each operative method". These items are referred to as equipment and medicine preparation information. The room-entry check list also includes, as a check item, "marking". This item is referred to as marking information.

FIG. 10 is an example of display contents of a sign-in check list. One field of the display contents indicates one check item.

The sign-in check list includes, as a check item, "surgical site marked?". This item is referred to as marking information. The sign-in check list also includes, as check items, "anesthetic machine and medicine check completed?" and "pulse oximeter attached to patient and in operation?". These items are referred to as equipment and medicine check information. The sign-in check list also includes, as check items, "patient have known allergy?", "patient has a risk of difficulty in airway control or accidental ingestion?", and "hemorrhage risk of patient is 500 ml (7 ml/kg for children) or more?". These items are referred to as patient's risk information.

FIG. 11 is an example of display contents of a time-out check list. One field of the display contents indicates one check item.

The time-out check list includes, as a check item, "scheduled surgery time?". This item is referred to as schedule information. In a case where the surgery schedule is associated with the related information, namely the items of an operation sheet or an electronic medical record, the operating room system 200 displays the scheduled surgery time on the terminal after the time-out check. When there is no association like that described above, the operating room system 200 displays on the terminal the total time of manipulation steps of the operative method selected for the surgery. The time-out check list includes, as check items, "estimated hemorrhage amount?", and "any concern about procedure and patient?". These items are referred to as estimated surgery progress information. In a case where the surgery schedule is associated with the related information, namely the items of an operation sheet or an electronic medical record, the operating room system 200 displays the estimated hemorrhage amount on the terminal after the time-out check. The time-out check list also includes, as a check item, "prophylactic antimicrobial administration was done within latest 60 minutes?". This item is referred to as medicine preparation information. The time-out check list also includes, as a check item, "sterilization of instrument was confirmed?". This is item is referred to as equipment preparation information.

FIG. 12 is an example of display contents of a sign-out check list. One field of the display contents indicates one check item.

The sign-out check list includes, as a check item, "name of patient, name of disease, name of operative method?". This item is referred to as patient and surgery identification information. In a case where the surgery schedule is associated with the related information, namely the items of an operation sheet or an electronic medical record, the operating room system 200 displays the name of patient, the name of disease, the name of operative method on the terminal after the sign-out check. The sign-out check list also includes, as a check item, "numbers of equipment, gauzes (sponges) and needles are correct?". This item is referred to as information of number of equipment. The sign-out check list also includes, as check items, "pulse oximeter attached to patient and in operation?", and "any equipment issues to handle?". These items are referred to as equipment operation information. The sign-out check list also includes, as a check item, "display of specimen". This item is referred to as specimen information. The sign-out check list also includes, as a check item, "any key concerns in post-surgery recovery or management of patient?". This item is referred to as estimated post-surgery progress information.

2. First Detailed Configuration Example

Heretofore, confirmation using a check list has been performed in surgery in order to reduce risks of confirmation error in surgery, such as misidentification of patient or misidentification of surgical site. An object thereof is to appropriately present information to the members in charge of the confirmation since the members in charge of sign-in, the members in charge of time-out, and the members in charge of sign-out are different upon room entry.

The International Publication No. WO2019/116593 mentioned above discloses a surgery-related information presentation device that presents navigation information for supporting surgery, such as surgical procedures and risk information, to a user. It may be effective to add a check list input function to such a surgery-related information presentation device; however, since some members of the surgery team do not perform check list input, presenting the same check list screen to all members may result in unnecessary information presentation, and may decrease convenience.

The first detailed configuration example was made in light of such a situation, and makes it possible to efficiently support check list input in surgery by operation team members. The first detailed configuration example is described below.

FIG. 13 is an example of members in charge of each check list. The circle ("o") indicates a member or members having a terminal in which the check list is displayed, and that the member(s) can operate the check list from his/her terminal. The cross ("x") indicates a member or members having a terminal in which the check list is not displayed, and that the member(s) cannot operate the check list from his/her terminal. For example, the operating room system 200 determines the correspondence between the member and the terminal based on ID authentication or the like in the terminal. Although the check list is displayed on the terminals of members marked with "x", the members may be incapable of operation of the check list from his/her terminal.

The room-entry check list is displayed on the first terminal 221 of the circulating nurse, and the circulating nurse can operate the room-entry check list. The other members cannot operate the room-entry check list.

The sign-in check list is displayed on the first terminal 221 of the circulating nurse and the third terminal 223 of the anesthesiologist, and the circulating nurse and the anesthesiologist can operate the sign-in check list. The other members cannot operate the sign-in check list.

The time-out and sign-out check lists are displayed on the first terminal 221 of the circulating nurse, the second terminal 222 of the scrub nurse, the third terminal 223 of the anesthesiologist, and the monitor viewed by the surgeon, and the circulating nurse, the scrub nurse, the anesthesiologist, and the surgeon can operate the time-out check list. The monitor viewed by the surgeon is, for example, a support monitor 251. If the surgeon has no input means, for example, if the support monitor 251 has no touch panel on it, the surgeon may verbally deliver it to another member, making him/her input the information to the check list from his/her terminal.

The surgical support system 50 according to the present embodiment described above includes the information processing system 210. The information processing system 210 includes the processor 211. The processor 211 establishes communication connection with a plurality of terminals including the first terminal 221 for displaying information to a first member 291 who plays a first role among the operation team members, and the second terminal 222 for displaying information to a second member 292 who plays a second role among the operation team members. The processor 211 performs processing of displaying on the first terminal 221 a first check list that requires input before start of the surgical support by the surgical support system 50 to present the first check list to the first member. When accepting input to the first check list from the first member 291 via the first terminal 221, the processor 211 performs processing of displaying on the first terminal 221 the first check list, the check status of which is changed in accordance with the accepted input. The processor 211 does not accept change of a check status of the first check list from the second member 292.

According to the present embodiment, since the presentation of the first check list and the acceptance of the check input can be appropriately controlled in accordance with the roles of the first member and the second member, it is possible to efficiently support the check list inputs by the operation team members. For example, the first member who plays a role of checking the first check list can perform the input to the first check list, and the second member who does not need to check the first check list can perform works other than the check list input, such as operation of the supplementary region.

In the example of FIG. 13, the first member 291 having the first role is a circulating nurse, and the second member 292 having the second role is a scrub nurse. The first check list is a sign-in check list. The change and sharing of the check statuses and the "process of display" are described in FIG. 8.

In the present embodiment, the plurality of terminals include the third terminal 223 for presenting information to the third member 293 who plays the third role among the operation team members. The processor 211 presents the first check list to the first member 291 and the third member 293 by performing processing of displaying the first check list on the first terminal 221 and the third terminal 223. When accepting at least one of input to the first check list from the first member via the first terminal 221 or input to the first check list from the third member 293 via the third terminal 223, the processor 211 performs processing of displaying on the first terminal 221 and the third terminal 223 the first check list, the check status of which is changed in accordance with the accepted input.

According to the present embodiment, since it is possible to appropriately control the presentation of the first check list and the acceptance of the check input in accordance with the roles of the first to third members, it is possible to efficiently support the check list inputs by the operation team members.

In the example of FIG. 13, the third member 293 having the third role is an anesthesiologist.

Further, in the present embodiment, the processor 211 does not allow the second terminal 222 to display the first check list, thereby inhibiting acceptance of change of check status of the first check list from the second member 292.

According to the present embodiment, since the first check list is not displayed on the second terminal, the second member cannot change the first check list. This enables to inhibit acceptance of change of check status of the first check list from the second member.

For example, the following first and second methods may be used as the method of "inhibiting acceptance of change of check status".

In the first method, the processor 211 does not accept input to the first check list from the second member 292 via the second terminal 222, thereby inhibiting acceptance of change of check status of the first check list from the second member 292.

More specifically, regardless of whether or not the first check list is displayed on the second terminal 222, the processor 211 rejects any check inputs from the second member 292 to the second terminal 222. This inhibits acceptance of change of check status of the first check list from the second member.

In the second method, when accepting input to the first check list from the second member 292 via the second terminal 222, the processor 211 does not change the check status in accordance with the accepted input, thereby inhibiting acceptance of change of check status of the first check list from the second member.

More specifically, although the first check list is displayed on the second terminal 222, and check input to the second terminal 222 by the second member 292 can be accepted, the processor 211 does not reflect the accepted input on the check status. This enables to inhibit acceptance of change of check status of the first check list from the second member.

Further, in the present embodiment, the processor 211 does not accept change of check status of the first check list from the surgeon 294 among the operation team members.

According to the present embodiment, since it is possible to appropriately control the presentation of the check list and the acceptance of the check input in accordance with the roles of the first to third members operating the terminals and the surgeon watching the monitor, it is possible to efficiently support the check list inputs by the operation team members.

In the present embodiment, the processor 211 does not display the first check list on the monitor 251 for presenting information to the surgeon 294 among the operation team members, and thus does not accept change of check status of the first check list from the surgeon 294.

According to the present embodiment, since the first check list is not displayed on the monitor viewed by the surgeon, the surgeon cannot change the first check list. This enables to inhibit acceptance of change of check status with respect to the first check list from the surgeon.

In the present embodiment, the first check list requires input before administration of anesthesia.

The check list that requires input before administration of anesthesia is the sign-in check list. According to the present embodiment, it is possible to appropriately control the presentation of the check list that requires input before administration of anesthesia and also control the acceptance of the check input in accordance with the roles of the members operating the terminals.

Further, in the present embodiment, the processor 211 performs processing of displaying on the first terminal 221 and the second terminal 222 a second check list that requires input before the start of the surgical support by the surgical support system after the completion of input to the first check list to present the second check list to the first member 291 and the second member 292. When accepting at least one of input to the second check list from the first member 291 via the first terminal 221 or input to the second check list from the second member 292 via the second terminal 222, the processor 211 performs processing of displaying on the first terminal 221 and the second terminal 222 the second check list, the check status of which is changed in accordance with the accepted input.

According to the present embodiment, since the presentation of the second check list and the acceptance of check list input can be appropriately controlled in accordance with the roles of the first member and the second member, it is possible to efficiently support the check list inputs by the operation team members.

In the example of FIG. 13, the second check list is a time-out check list.

Further, in the present embodiment, the processor 211 displays the second check list on the first terminal 221, the second terminal 222, the third terminal 223, and the monitor 251 for presenting information to the surgeon 294 to present the second check list to the first member 291, the second member 292, the third member 293, and the surgeon 294. When accepting input to the second check list from at least one of the first member 291 via the first terminal 221, the second member 292 via the second terminal 222, the third member 293 via the third terminal 223, or the surgeon 294 via the monitor 251, the processor 211 performs processing of displaying on the first terminal 221, the second terminal 222, the third terminal 223, and the monitor 251 the second check list, the check status of which is changed in accordance with the accepted input.

According to the present embodiment, since the presentation of the second check list and the acceptance of check list input can be appropriately controlled in accordance with the roles of the first to third members and the surgeon, it is possible to efficiently support the check list inputs by the operation team members.

Further, in the present embodiment, the processor 211 performs processing of displaying on the first terminal 221 and the second terminal 222 a third check list that requires input after end of the surgical support to present the third check list to the first member 291 and the second member 292. When accepting at least one of input to the third check list from the first member 291 via the first terminal 221 or input to the third check list from the second member 292 via the second terminal 222, the processor 211 performs processing of displaying on the first terminal 221 and the second terminal 222 the third check list, the check status of which is changed in accordance with the accepted input.

According to the present embodiment, since the presentation of the third check list and the acceptance of check list input can be appropriately controlled in accordance with the roles of the first member and the second member, it is possible to efficiently support the check list inputs by the operation team members.

In the example of FIG. 13, the third check list is a sign-out check list.

Further, in the present embodiment, the processor 211 displays the third check list on the first terminal 221, the second terminal 222, the third terminal 223, and the monitor 251 for presenting information to the surgeon 294 to present the third check list to the first member 291, the second member 292, the third member 293, and the surgeon 294. When accepting input to the third check list from at least one of the first member 291 via the first terminal 221, the second member 292 via the second terminal 222, the third member via the third terminal 223, or the surgeon 294 via the monitor 251, the processor 211 performs processing of displaying on the first terminal 221, the second terminal 222, the third terminal 223, and the monitor 251 the third check list, the check status of which is changed in accordance with the accepted input.

According to the present embodiment, since the presentation of the third check list and the acceptance of check list input can be appropriately controlled in accordance with the roles of the first to third members and the surgeon, it is possible to efficiently support the check list inputs by the operation team members.

The present embodiment may also be performed as a surgical support method as described below. The surgical support method may be performed as a method of operating the surgical support system 50. The surgical support method includes performing processing of displaying on the first terminal 221 the first check list that requires input before the start of the surgical support by the surgical support system 50 to present the first check list to the first member 291 who plays the first role among the operation team members. Further, when accepting input to the first check list from the first member 291 via the first terminal 221, the surgical support method includes performing processing of displaying on the first terminal 221 the first check list, the check status of which is changed in accordance with the accepted input. The surgical support method also includes inhibiting acceptance of change of check status of the first check list from the second member 292 who plays the second role among the operation team members.

Moreover, the present embodiment may be implemented as a program or a computer-readable non-transitory information storage medium, as described below. The program causes a computer to execute processing of displaying on the first terminal 221 the first check list that requires input before the start of the surgical support by the surgical support system 50 to present the first check list to the first member 291 who plays the first role among the operation team members. Further, when accepting input to the first check list from the first member 291 via the first terminal 221, the program causes a computer to execute processing of displaying on the first terminal 221 the first check list, the check status of which is changed in accordance with the accepted input. The surgical support method also causes a computer to execute inhibiting acceptance of change of check status of the first check list from the second member 292 who plays the second role among the operation team members. The information storage medium stores the program. The computer reads out the program from the information storage medium and executes the program, thereby realizing the functions of the surgical support system 50. The information storage medium can be implemented by, for example, an optical disc, a memory card, an HDD, a semiconductor memory, or the like. The semiconductor memory is, for example, a ROM or a nonvolatile memory.

Figure 14:
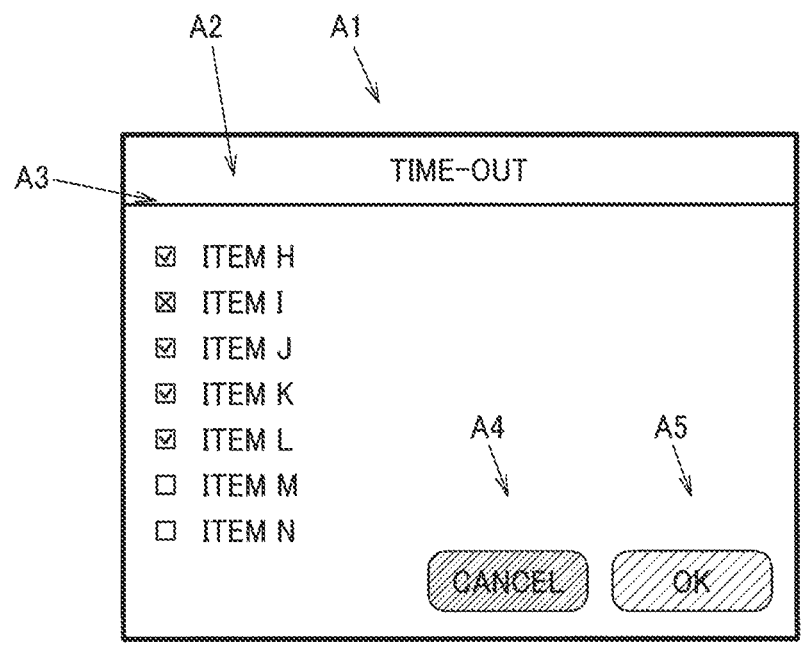
FIG. 14 is an example of check list screen displayed on a terminal.

FIG. 14 is an example of check list screen displayed on a terminal. In the figure, time-out is illustrated as an example.

As shown in A1, the check list name is displayed in an upper portion of the screen. As shown in A2, items H to N are arranged from top to bottom under the check list name. However, the number and the arrangement of the items are not limited to those shown in the figure. As shown in A3, a check box is displayed at the head of each item. The check box is displayed in a mode corresponding to the check status, and the check status is shared among the terminals on which the time-out check list is displayed.

As shown in A4, a cancel button is displayed in a lower portion of the screen. The cancel button can be pressed by, for example, a tap operation on the touch panel. The cancel button is used to cancel the check list screen for moving to another screen. The cancel button is in a state of being able to be pressed regardless of the progress of the check.

As shown in A5, a OK button is displayed in a lower portion of the screen. The OK button can be pressed by, for example, a tap operation on the touch panel. The OK button is used to complete the check of the check list for moving to another screen. When all the items have not been checked, the OK button is grayed out and is in an inactive state. When all items have been checked, the gray-out of the OK button is removed, making the OK button active.

For example, when the check of the room-entry check list is completed and the OK button is pressed, the sign-in check list is displayed on the first terminal 221 and the third terminal 223. When the check of the sign-in check list is completed and the OK button is pressed, a time-out check list is displayed on the first to third terminals 221-223 and the support monitor 251. When the check of the time-out check list is completed and the OK button is pressed, a live image of the surgery and assistance information for performing a supplementary operation for surgery are displayed on the first to third terminals 221-223. Further, the surgical support information described in, for example, step S2 in FIG. 6 is displayed on the support monitor 251. When the surgery ends, a sign-out check list is displayed on the first to third terminals 221-223 and the support monitor 251. When the check of the sign-out check list is completed and the OK button is pressed, the check ends.

Figure 15:
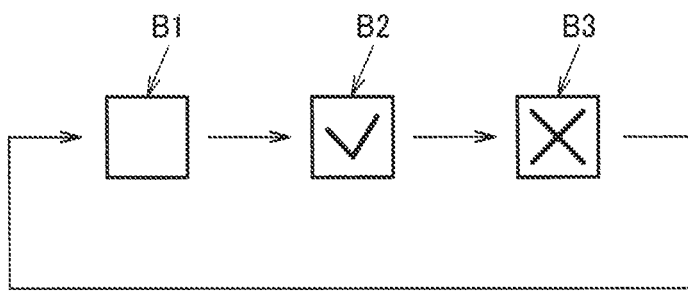
FIG. 15 is an example of display mode of check box.

FIG. 15 shows an example of display mode of check box. As shown in B1, in the initial state, the check box is in a first display mode indicating an unchecked state. For example, in the first display mode, the check box is blank.

When one of the members capable of checking the check list taps the check box, the check box changes to a second display mode indicating that the check box has been checked, as shown in B2. For example, in the second display mode, the check box has a check mark. In addition, the check box may also be colored. The color is, for example, light blue.

When one of the members capable of checking the check list further taps the check box, the check box changes to a third display mode indicating an objection state as shown in the B3. The objection state indicates that the members have different opinions on the check item. For example, in the third display mode, the check box has an X mark. Further, the check box may also be colored with a color different from that in the second display state. The color is, for example, yellow.

When one of the members capable of checking the check list further taps the check box, the check box returns to the first display mode as shown in B1.

In the present embodiment described above, when a first check item in the first check list is displayed in the first display state on the first terminal 221 and the third terminal 223, the processor 211 performs processing of changing the display state of the first check item to the second display state that is different from the first display state in accordance with the input and displaying the first check item in the second display state on the first terminal 221 and the third terminal 223. The input herein means at least one of the input to the first check item from the first member 291 via the first terminal 221 or the input to the first check item from the third member 293 via the third terminal 223.

In the present embodiment, when the first check item is displayed on the first terminal 221 and the third terminal 223 in the second display state, the processor 211 performs processing of changing the display state of the first check item to a third display state that is different from the first or second display state in accordance with the input and displaying the first check item in the third display state on the first terminal 221 and the third terminal 223. The input herein means at least one of the input to the first check item from the first member 291 via the first terminal 221 or the input to the first check item from the third member 293 via the third terminal 223.

According to the present embodiment, regardless of which of the first member and the third member checks the first check item, the first check item changes from the first display state to the second display state or from the second display state to the third display state. This enables both the first member and the third member to change the check status of the check list, and the modified check status is shared between the first member and the third member.

Further, in the present embodiment, the first display state indicates that the first check item is unchecked. The second display state indicates that the first check item has been checked. The third display state indicates that the first check item is in an objection state.

According to the present embodiment, when the first or third member checks the first check item, the display state of the first check item can be sequentially changed to the state of "unchecked", "checked", and "objection". Since this display state is shared between the first member and the third member, it is possible to share the intentions of both members.

Further, in the present embodiment, the processor 211 presents a button for moving to the next screen after the input to the first check list is completed to the first member 291 and the third member 293 by performing processing of displaying the button on the first terminal 221 and the third terminal 223. When accepting at least one of input to the button from the first member 291 via the first terminal 221 or input to the button from the third member 293 via the third terminal 223, the processor 211 performs processing of displaying the next screen on the first terminal 221 and the third terminal 223.

According to the present embodiment, the first member and the third member can operate the button after the input to the first check list is completed to thereby move the display of the terminal to show the next screen.

In the example of FIG. 14, the "button for moving to the next screen" is the OK button A5, and the "process of displaying the button on the terminal" means that the OK button is changed from the gray-out state to the active state. However, the present disclosure is not limited to this example, and may be arranged such that the OK button is not displayed when the input to the first check list has not been completed, and is displayed only when the input to the first check list has been completed.

Further, in the present embodiment, the processor 211 performs processing of displaying on the monitor 251 surgical support information for performing surgical support for the surgeon among the operation team members after the input to the second check list is completed.

The second check list is a time-out check list and is checked before skin incision. By automatically moving to surgical support after the completion of input to the second check list, it is possible to efficiently support the operation team members.

The transition to the surgical support after the time-out is described, for example, in steps S26 and S27 in FIG. 7. The surgical support information is described, for example, in step S2 of FIG. 6.

Further, in the present embodiment, the processor 211 performs processing of recording the completion of input to the second check list. Specifically, the processor 211 performs processing of recording the completion of input to the second check list on the storage device 212 of the operating room system 200 or the storage device 112 of the staff station system 100.

The second check list is a time-out check list. Ending time-out and starting surgery is one of the milestones in a surgery flow. According to the present embodiment, it is possible to record milestones in such a surgery flow. For example, the recorded information can be used by the surgical support system 50 as surgery history information.

Further, in the present embodiment, the processor 211 presents a fourth check list that requires input before checking the first check list to the first member 291 by performing processing of displaying the fourth check list on the first terminal 221. The processor 211 accepts an input to the fourth check list from the first member 291 via the first terminal 221. The processor 211 performs processing of displaying the first check list on the first terminal 221 after the input to the fourth check list is completed.

According to the present embodiment, the first check list is a check list to be checked after the checking of the fourth check list is completed. After the input to the fourth check list is completed, the first check list may be automatically displayed on the first terminal 221 to efficiently support the operation team members.

3. Second Detailed Configuration Example

The International Publication No. WO2019/116593 mentioned above discloses a surgery-related information presentation device that presents navigation information for supporting surgery to a user. In such a previously-known system, support information is displayed to a surgery operator during the surgery, thereby enabling various types of information support by switching the display setting. However, the previously-known system assumes that all members view the same display; that is, the system allows switching of display contents only in a single terminal. The previously-known system does not have a function allowing each member to confirm different information items depending on their roles, and thus has a drawback of being incapable of efficient information support for a plurality of team members.

Specifically, a surgery generally cannot be completed only by a work of a surgeon, but also includes planning, preparation, support, and the like, which are performed by a team of multiple members. The team members also include those outside the operating room. It is therefore desirable that the surgical support system provides information support to all team members having such a wide variety of roles. On the other hand, since different information is required for each role, it is difficult to display all of them on a single terminal because the display region is limited. Moreover, even if all information items can be displayed, the screen becomes complicated, thereby decreasing the convenience. Further, in some cases, even if the members have the same role, the desired information amount and display form are different depending on the skill and proficiency of the individual. Therefore, it is ideal to meet such needs.

The second detailed configuration example in light of such circumstances is described below.

Figure 16:
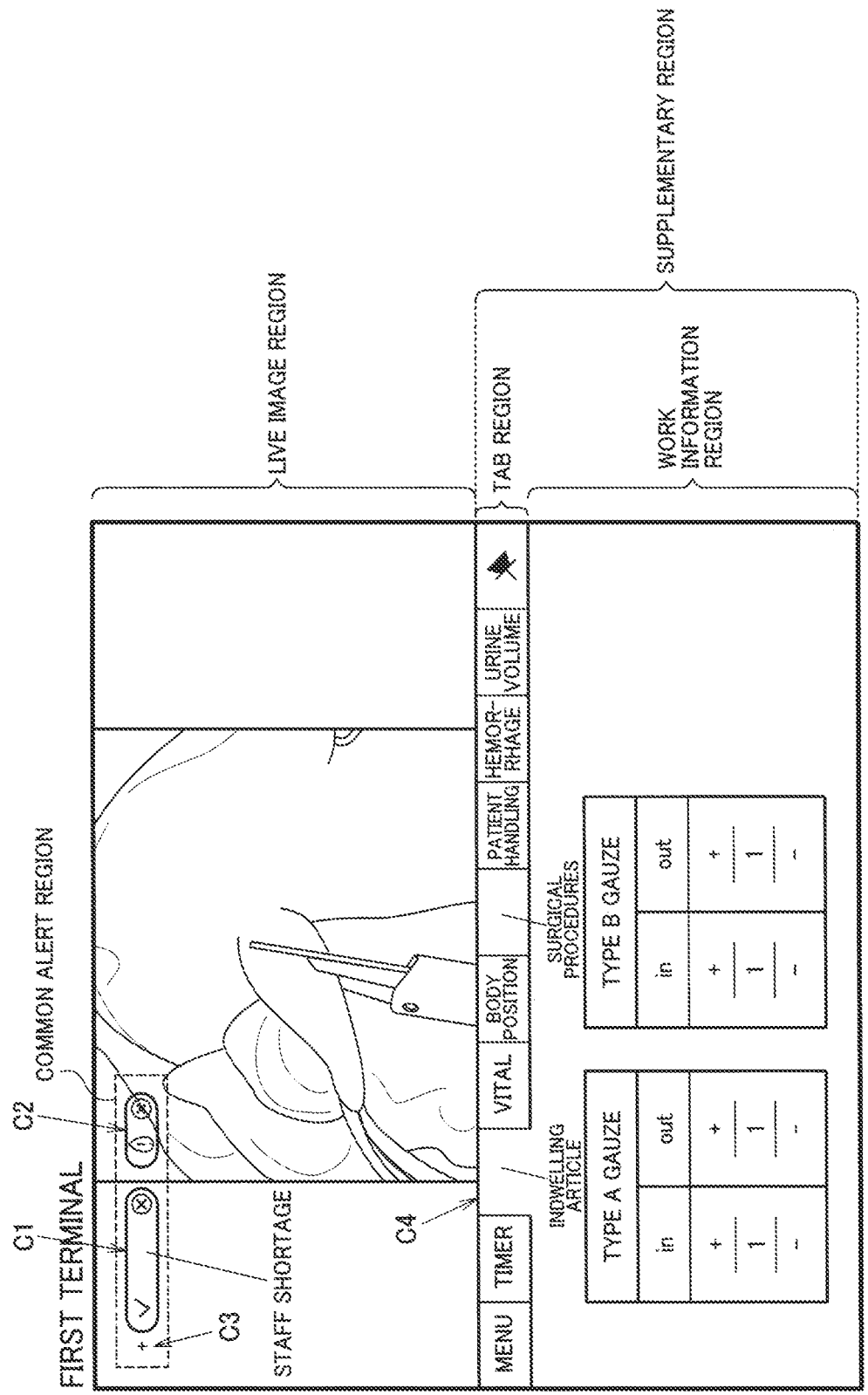
FIG. 16 is an example of screen displayed on the first to third terminals of an operating room system during surgery.

FIG. 16 is an example of screen displayed on the first to third terminals 221-223 of the operating room system 200 during surgery. The first to third terminals 221-223 can be independently operated.

A live image region is positioned on the upper side of the screen. The live image region displays the same live image as the endoscopic image displayed on the endoscope monitor 252 viewed by the surgeon 294. The live image is a real-time surgery image captured by an endoscope or the like. No support information is added to the live image.

A common alert region is positioned in a upper left portion of the live image region. Various types of alert are displayed in the common alert region, and the same alert is displayed in the common alert region of the first to third terminals 221-223. FIG. 16 shows an example in which an alert indicating "staff shortage" and an alert indicating "hemorrhage detection" are displayed as shown in C1 and C2, respectively. An alert name and an X mark are displayed for each alert. When a member taps the X mark, the alert disappears. For example, the alert is notified to the staff station terminal 110, and a notification display for confirming the notification is displayed on each terminal of the operating room system 200. At this time, if a member desires to hide the alert superimposed on the live image, the member can hide the alert by tapping the X mark. For the staff shortage alert, a check mark is displayed in a predetermined case. Specifically, the staff shortage alert is notified to the staff station terminal 110 and displayed in the monitor 150 of the staff station terminal 110. When a staff in the staff station 10 confirms the staff shortage alert shown in the monitor 150 and taps the alert, a check mark is displayed on the staff shortage alert shown in each terminal of the operating room system 200. At this time, if a member taps the X mark of the staff shortage alert, the staff shortage alert is cancelled, and the staff shortage alert disappears also in the monitor 150 of the staff station terminal 110.

In addition to these alerts, an alert indicating a shortage of blood transfusion pack, an alert indicating an excess of scheduled surgery time, an alert indicating abnormal body position, and the like are displayed in the common alert region. These common alerts are related to supplementary operation of tabs described later. For example, the hemorrhage detection alert relates to a hemorrhage tab and the abnormal body position alert relates to a body position tab. However, the common alerts may include an alert irrelevant to supplementary operation of a tab. The common alerts include those automatically displayed based on detection results of various sensors or recognition results of the image recognition process, as well as those manually added by tapping "+" mark shown in C3. The details of these alerts are described later.

A supplementary region is positioned on the lower side of the screen. A tab region is positioned above the supplementary region, and a work information region is positioned below the tab region. In the tab region, a plurality of tabs are arranged side by side in the horizontal direction. The tabs are selectable by tapping on it. In the tab region, for example, tabs of "menu", "timer", "indwelling article", "vital", "body position", "surgical procedures", "patient handling", "hemorrhage", "urine volume", and "pin" are displayed. However, the type of the tab is not limited to them. When one of the tabs is selected, work information corresponding to the selected tab is displayed in the work information region. FIG. 16 shows a state in which the "indwelling article" tab shown in C4 is selected.

A counter for counting indwelling articles as "indwelling article" work information is displayed. FIG. 16 shows a state in which counters respectively corresponding to "type A gauze" and "type B gauze" are displayed. However, the indwelling article to be counted is not limited to gauze. The name of indwelling article is attached to each counter. An "in" counter for counting indwelling articles inserted into the body and an "out" counter for counting indwelling articles taken out from the body are displayed. A "+" button for incrementing the count value, the count value, and a "−" button for decrementing the count value are displayed in the "in" counter and the "out" counter.

The "pin" tab is used to immobilize a tab, which is usually called a bookmark function. The "pin" tab is used to select an arbitrary tab, making it fixedly appear on the screen. For example, if "vital" is set as the "pin" tab, it is possible to make "vital" constantly appear by selecting the "pin" tab. With the "pin" tab, two tabs can be fixedly displayed. Specifically, the work information in the first tab is displayed to the left of the work information region, and the work information in the second tab is displayed to the right of the work information region. Any tabs can be set as the first tab and the second tab. Since these two types of work information in the two tabs can be viewed side by side, an efficient supplementary operation can be performed. It may also be arranged such that three or more tabs are fixedly displayed in the "pin" tab.

The surgical support system 50 according to the present embodiment described above includes the processor 211. The processor 211 establishes communication connection with a terminal and performs processing of displaying a display screen on the terminal to present the display screen to members other than the surgeon 294 among the operation team members via the terminal. The display screen includes a live image region and a supplementary region. In the live image region, a live image of a surgery conducted by the operation team member is displayed. In the supplementary region, information regarding a supplementary operation, which is selected from among a plurality of supplementary operations for managing the surgery in response to selection and input from a member via a terminal, is displayed.

According to the present embodiment, since the information regarding the supplementary operation selected by the selection and input from the member via the terminal is displayed in the supplementary region, each member can confirm different information for each role. This makes it possible to perform efficient information support for a plurality of team members.

In the example of FIG. 4, the "terminal" may be any one of the first to third terminals 221-223, given that the surgical support system 50 includes at least one terminal. The action of "selection and input from a member via a terminal" corresponds to an operation of selecting a tab in the example of FIG. 16. However, the action of "selection and input from a member via a terminal" is not limited to the tab operation, insofar as it is an operation of selecting information displayed in the supplementary region.

Further, in the present embodiment, a live image displayed on the monitor 252 of the surgeon is displayed in the live image region.

According to the present embodiment, each member can view the same live image as that displayed on the monitor of the surgeon on each terminal. Thus, the surgery state is shared among the operation team members by allowing them to view the same display of live image.

In addition, in the present embodiment, in the case where the terminal is the first terminal 221 and the member is the first member 291, the processor 211 establishes communication connection with the first terminal 221 that displays information to the first member 291 and the second terminal 222 that displays information to the second member 292 among the operation team members, and performs processing of displaying a display screen on the first and second terminals 221 and 222. In the supplementary region of the first terminal 221, information regarding a supplementary operation selected among a plurality of supplementary operations in response to selection and input from the first member 291 via the first terminal 221 is displayed. In the supplementary region of the second terminal 222, information regarding a supplementary operation selected among a plurality of supplementary operations in response to selection and input from the second member 292 via the second terminal 222 is displayed.

According to the present embodiment, each member can arbitrary select information and display it in the supplementary region. This makes it possible to allow each member to confirm different information for each role, thereby performing efficient information support for a plurality of team members.

Further, in the present embodiment, the display screen has a common alert region. The common alert region displays a common alert related to at least one supplementary operation among the plurality of supplementary operations outside the supplementary region, regardless of which one of the supplementary operations has been selected from among the plurality of supplementary operations by the selection and input.

According to the present embodiment, even in a state in which each member selects arbitrary information to be displayed in the supplementary region, the common alert is displayed in the common alert region so that the common alert is shared among all members. Thus, information that needs to be shared regardless of the role is shared among all members.

Further, in the present embodiment, the supplementary region includes a tab region and a work information region. A plurality of tabs are arranged in the tab region, and respective tabs are given different supplementary operations among a plurality of supplementary operations. The work information region displays information regarding the supplementary operation allocated to the tab selected among the plurality of tabs by selection and input.

According to the present embodiment, the member can switch information to be displayed in the work information region by selecting a tab displayed on the terminal. Each member can independently select a tab, and therefore each member can confirm different information for each role.

Further, in the present embodiment, the plurality of tabs include first to n-th (n is an integer of 2 or more) tabs in which first to n-th supplementary operations are allocated, and a fixed display tab in which one or more supplementary operations among the first to n-th supplementary operations are set as supplementary operations that are fixedly displayed. When one of the first to n-th tabs is selected by selection and input, the work information region displays information regarding the supplementary operation allocated to the selected tab. When the fixed display tab is selected by selection and input, the work information region displays information regarding the supplementary operation (s) for the fixed display.

According to the present embodiment, each member can assign information of the supplementary operation(s) for which the member desires to check frequently to the fixed display tab. Since each member is free to allocate any supplementary operation to the fixed display tab, each member with a different role can confirm different information depending on which information he/she desires to check frequently.

The present embodiment may be performed as a surgical support method as described below. The surgical support method may be performed as a method of operating the surgical support system 50. The surgical support method includes performing processing of displaying a display screen having a live image region and a supplementary region on a terminal to present the display screen via the terminal to members other than the surgeon 294 among the operation team members. The surgical support method also includes displaying a live image of the surgery conducted by the operation team members in the live image region of the display screen. In addition, the surgical support method includes displaying information regarding a supplementary operation, which is selected from among a plurality of supplementary operations for managing the surgery in response to selection and input from a member via a terminal, in the supplementary region of the display screen.

Moreover, the present embodiment may be implemented as a program or a computer-readable non-transitory information storage medium, as described below. The program causes a computer to execute processing of displaying a display screen having a live image region and a supplementary region on the terminal to present the display screen via the terminal to members other than the surgeon 294 among the operation team members. The program also causes a computer to execute display of a live image of the surgery conducted by the operation team members in the live image region of the display screen. In addition, the program causes a computer to execute display of information regarding a supplementary operation, which is selected from among a plurality of supplementary operations for managing the surgery in response to selection and input from a member via a terminal, in the supplementary region of the display screen. The information storage medium stores the program. The computer reads out the program from the information storage medium and executes the program, thereby realizing the functions of the surgical support system 50.

FIG. 17 shows an example of display mode according to skill or proficiency level. In each of the first to third terminals 221-223, it is possible to select a display mode according to skill or proficiency level. The display mode is switchable by, for example, a button operation, a swipe operation, or the like using a touch panel. FIG. 17 shows an example in which a screen for beginners is displayed on the first terminal 221 and a screen for experts is displayed on the second terminal 222.

Similar to FIG. 16, the screen for beginners displays the live image region, the common alert region, the tab region, and the work information region.

The screen for experts displays the live image region, the common alert region, and the tab region. The tab region is provided in a lower portion of the screen, and the work information region is not displayed. Therefore, the supplementary region of the screen for experts is smaller than the supplementary region of the screen for beginners. On the other hand, since the live image on the screen for experts is made larger than that for the live image region of the screen for beginners, the live image displayed on the screen for experts is larger than the live image on the screen for beginners. When a tab is selected, a screen similar to the screen for beginners is displayed, and work information corresponding to the selected tab is displayed in the work information region.

In the present embodiment described above, it is possible to set a first display mode in which the tab region and the work information region are displayed in the supplementary region of the display screen and a second display mode in which the tab region is displayed in the supplementary region of the display screen and the work information region is not displayed. When the second display mode is set, the display range of the supplementary region is made smaller than the display range of the supplementary region in the first display region, and the display range of the live image region is made larger than the display range of the live image region in the first display region.

According to the present embodiment, information can be presented to each member in a display mode corresponding to the skill or proficiency level of each member. For example, for a beginner, a screen for beginners on which more supplementary operation information is displayed may be provided. In contrast, for an expert, a screen for experts in which the surgery state can be more easily confirmed by showing a live image may be provided.

In the example of FIG. 17, the first display mode corresponds to the screen for beginners, and the second display mode corresponds to the screen for experts.

Further, in the present embodiment, the display screen of the first terminal 221 displays a display mode among the first display mode and the second display mode in accordance with setting input from the first member 291 via the first terminal 221. The display screen of the second terminal 222 displays a display mode among the first display mode and the second display mode in accordance with setting input from the second member via the second terminal 222.

According to the present embodiment, each member can set an arbitrary display mode. Thus, it is possible to present information to each member in a display mode corresponding to the skill or proficiency level of the member.

Figure 18:
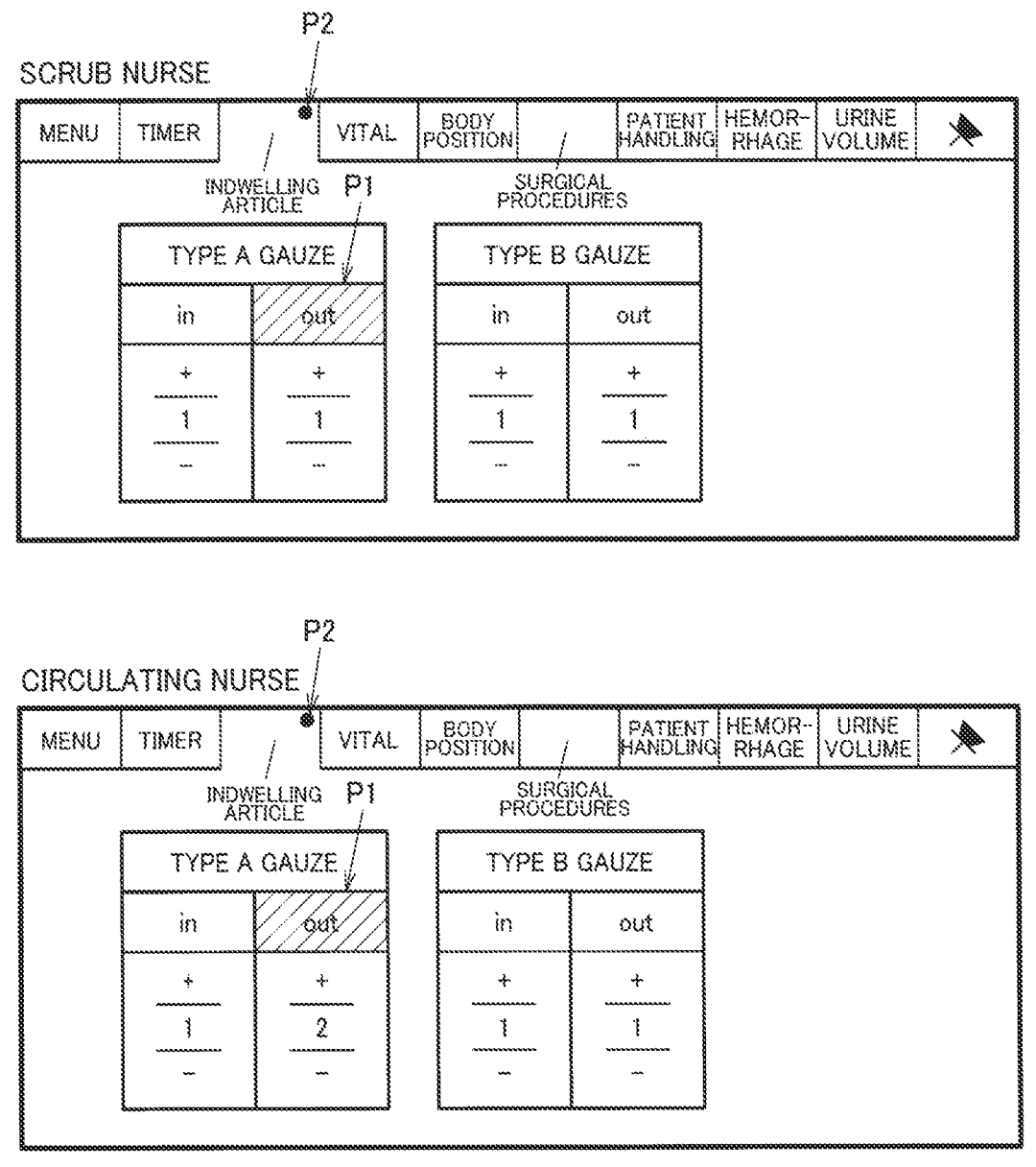

FIG. 18 shows an example of alert sign during the indwelling article count. This example describes an "out" counter in taking out type A gauze from the body by the circulating nurse and the scrub nurse. The same can be said for the "in" counter or counters for other indwelling articles.

As shown in P1, if the count value of the "out" counter is inconsistent between the circulating nurse and the scrub nurse, an alert sign is displayed in the portion of the count name "out" at the top of the counter. For example, the portion of the count name "out" becomes, for example, yellow. Further, as shown in P2, an alert sign is also displayed on the indwelling article tab. For example, a yellow or another color circular mark is added to the tab. This alert sign is displayed on the indwelling article tab even when a tab other than the indwelling article tab is selected. When the count value of the "out" counter of the circulating nurse is the same as that of the scrub nurse, the alert sign in the portion of the count name "out" and the alert sign in the indwelling article tab disappear.

In the present embodiment described above, the processor 211 accepts the first input value input from the first member 291 to the supplementary region of the first terminal 221 and the second input value input from the second member 292 to the supplementary region of the second terminal 222 with respect to a specific supplementary operation among a plurality of supplementary operations. When the first input value and the second input value are different, the processor 211 performs processing of displaying an alert sign indicating the difference in the display screens of the first terminal 221 and the second terminal 222.

According to the present embodiment, an alert sign is notified to each member when the input values from the members are inconsistent with respect to a specific supplementary operation for which consistency of input values from the members is required. This enables each member to confirm whether or not the input values are consistent based on the alert sign.

In the example of FIG. 18, the specific supplementary operation corresponds to the indwelling article count. The first input value corresponds to the indwelling article count value input by the circulating nurse, and the second input value corresponds to the count value of the indwelling article counter input by the scrub nurse.

Further, in the present embodiment, the specific supplementary operation is at least one of an action of counting the number of articles inserted into the body of the patient or an action of counting the number of inserted articles collected from the body of the patient. The first input value and the second input value are count values in such counting actions.

According to the present embodiment, an alert sign is displayed when the "in" count values or the "out" count values with respect to articles inserted into the body are inconsistent between the members. Since the count value and the alert sign are shared among all members, it is possible to reliably count the articles inserted into the body or inserted articles collected from the body.

Further, in the present embodiment, the alert sign is displayed on a tab corresponding to the specific supplementary operation among the plurality of tabs.

According to the present embodiment, even if a tab different from the tab corresponding to the specific supplementary operation is selected, the alert sign is displayed on the tab corresponding to the specific supplementary operation. Accordingly, even when a supplementary operation other than the specific supplementary operation is performed, the alert sign is shared among all members.

Figure 19:
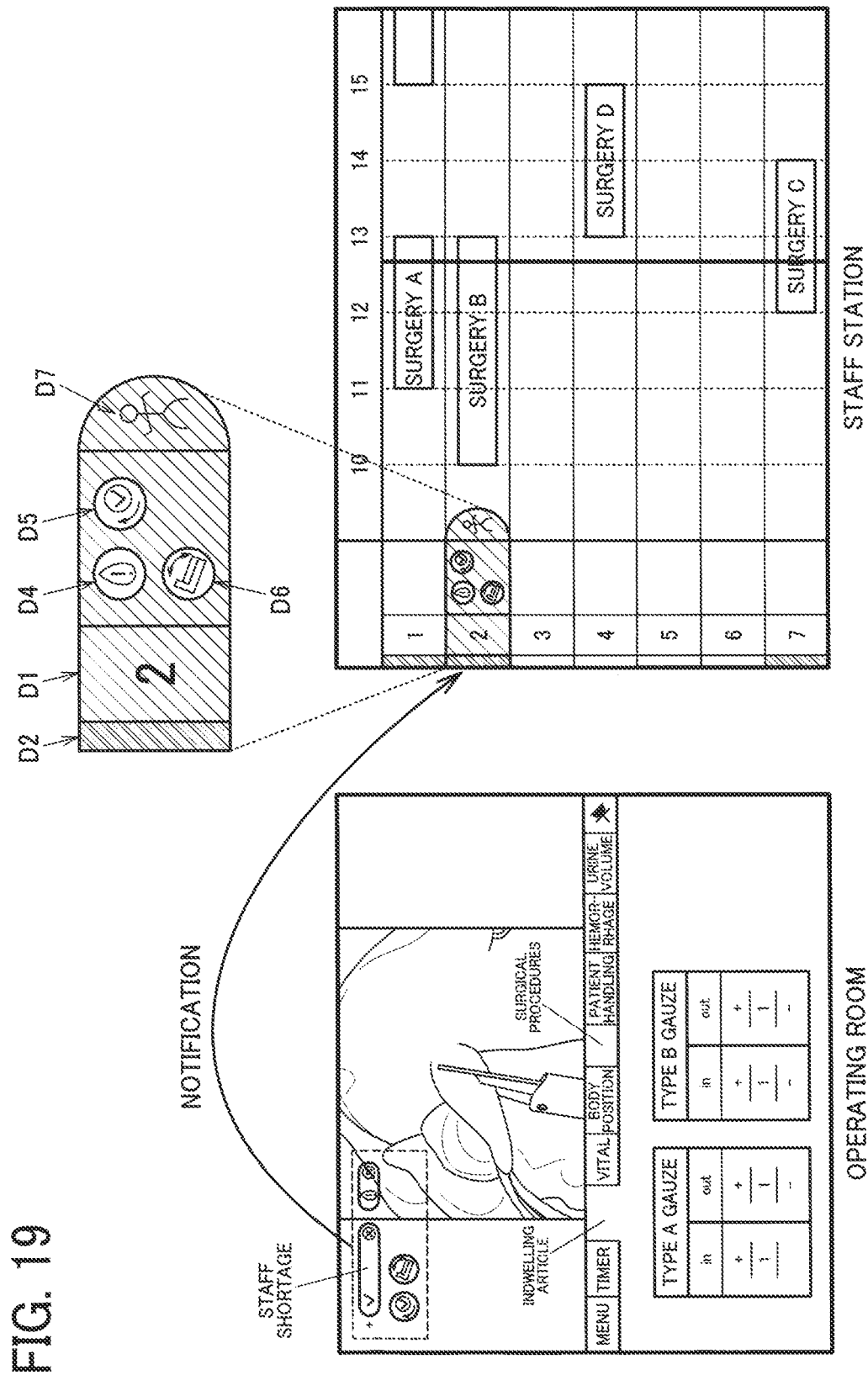
FIG. 19 is a diagram illustrating sharing of common alert for operating room and staff station.

FIG. 19 is a diagram illustrating sharing of common alert in the operating room and the staff station. The left figure shows a display screen displayed in a terminal in the operating room, and the right figure shows a schedule screen shown in the monitor 150 in the staff station.

The common alert displayed in the terminal in the operating room is also displayed on the monitor 150 in the staff station. Specifically, the processor 211 of the operating room system 200 transmits the information of the common alert to the staff station system 100 via the communication device 213. The processor 111 of the staff station system 100 receives the information of the common alert via the communication device 113 and displays an alert on the schedule screen based on the information.

The surgery schedule of each operating room is displayed on the schedule screen in the staff station. In the schedule screen, the operating room numbers are arranged along the vertical axis, and the time is indicated by the horizontal axis with a vertical line showing the current time. In FIG. 19, the vertical line is a thick solid line. A surgery plan bar indicating a scheduled surgery time of each surgery is displayed in the field of each operating room. FIG. 19 shows an example in which surgeries A to D are scheduled. In this example, information sharing between the operating room No. 2 in which surgery B is being performed and the staff station is described. However, similar information sharing is possible in other operating rooms.

The common alert notified from the operating room system 200 in the operating room No. 2 to the staff station system 100 is displayed in the field of the operating room No. 2 of the schedule screen. An enlarged view showing the vicinity of the region where the common alert is displayed is shown in the upper right figure. In the field of operating room, the operating room number is displayed as shown in D1. At the left end of the field, as shown in D2, a sign indicating that a surgery is being performed in that operating room is displayed. This sign is displayed when the scheduled surgery time in the surgery plan bar overlaps with the current time. As shown in D4 to D7, the display region of the common alert is positioned on the right side of the operating room number. D4 is an alert indicating hemorrhage detection, D5 is an alert indicating that the progress of surgery is behind schedule, D6 is an alert indicating abnormal body position, and D7 is an alert indicating staff shortage. D7 alert overlaps the area of the surgery plan bar. In a rectangular region where the alerts D4 to D6 are displayed in the display region of the common alert, up to four alerts can be displayed. There are priority orders of common alerts. When five or more common alerts are generated, four alerts are displayed in descending order of priorities. When one of the displayed four alerts is lifted, an alert having a higher priority among hidden alerts is newly displayed.

The alert indicating staff shortage is manually input from a terminal in the operating room.

An alert indicating hemorrhage detection is displayed based on the result of the image recognition process. Specifically, the processor 211 of the operating room system 200 recognizes hemorrhage according to the image recognition process performed on the live image, displays an alert of hemorrhage detection on a terminal in the operating room when hemorrhage is recognized from the live image, and notifies the staff station system 100 of alert information of hemorrhage detection.

The alert indicating behind schedule is displayed when the actual progress of surgery is behind the scheduled progress of the surgery set in association with the surgery plan bar. The processor 211 of the operating room system 200 determines the actual progress of surgery based on, for example, recognition of the scene shown in the live image, results of motion capture by an operation team member, or manual input by an operation team member. The processor 211 compares the actual progress of surgery with the scheduled progress acquired from the staff station system 100. When the actual progress of surgery is behind the scheduled progress, the processor 211 displays an alert indicating behind schedule on a terminal in the operating room, and notifies the staff station system 100 of alert information of behind schedule.

The alert indicating abnormal body position is displayed when it is determined that the body position of a patient having the surgery is abnormal. For example, an inclination sensor is provided in the operating table 260. When it is determined that the inclination of the operating table 260 is abnormal based on the detection result of the inclination sensor, the processor 211 of the operating room system 200 displays an alert indicating abnormal body position in a terminal of the operating room and notifies the staff station system 100 of alert information of the abnormal body position.

Figure 20:
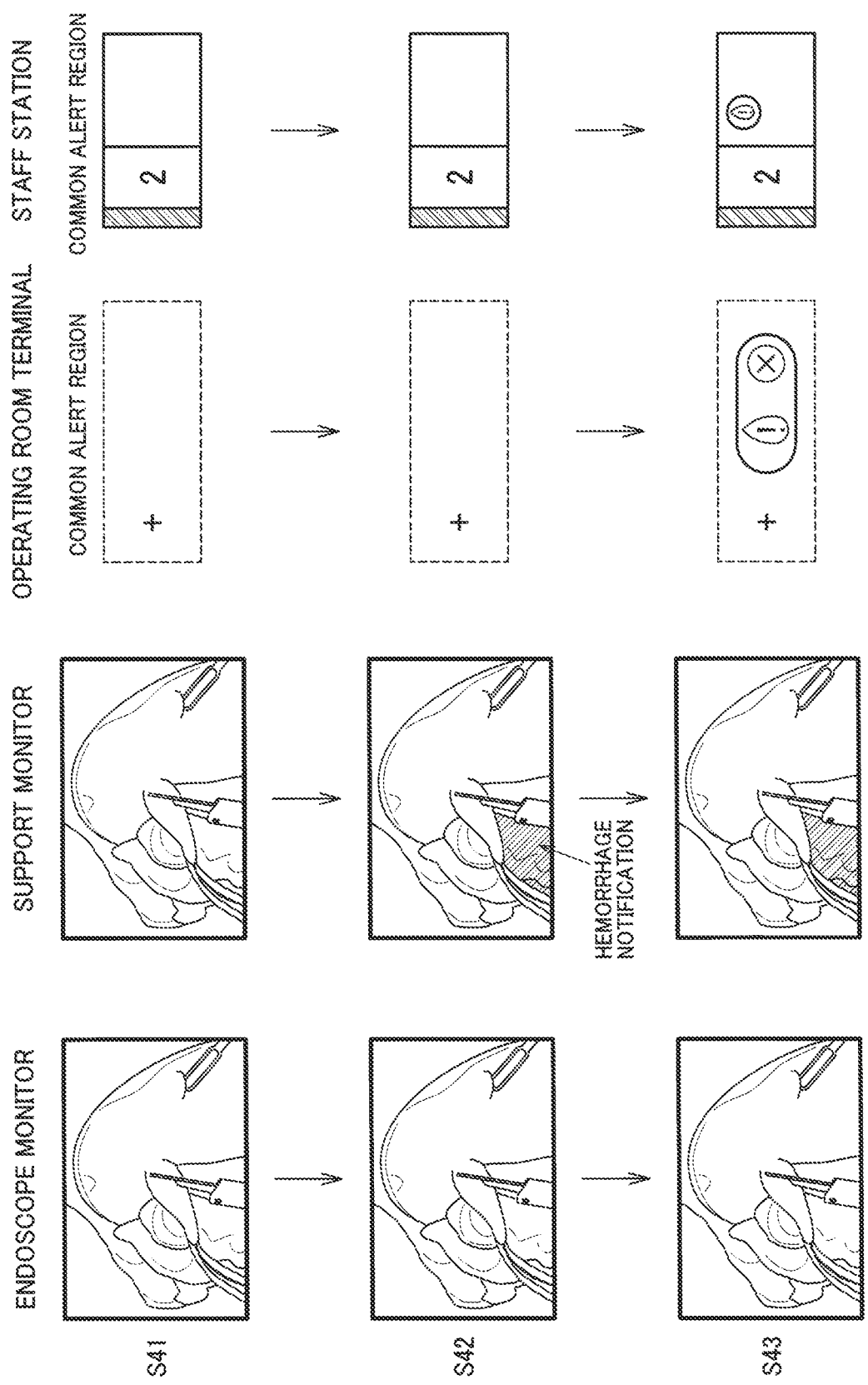
FIG. 20 is an example of display in the case of sharing a hemorrhage detection alert.

FIG. 20 shows an example of display in the case of sharing a hemorrhage detection alert. On the endoscope monitor 252, a live image of surgery is displayed as it is regardless of the result of hemorrhage detection.

As shown in step S41, when no hemorrhage is detected from the live image, the processor 211 of the operating room system 200 displays the live image as it is on the support monitor 251. The hemorrhage detection alert is not displayed on the terminal of the operating room and the schedule screen in the staff station.

As shown in step S42, when hemorrhage is detected from the live image, the processor 211 of the operating room system 200 displays on the support monitor 251 a highlighted display or the like indicating a hemorrhage area superimposed on the live image.

As shown in step S43, the processor 211 of the operating room system 200 displays on the terminal in the operating room a hemorrhage detection alert, and notifies the staff station system 100 of information of the hemorrhage detection alert. The processor 111 of the staff station system 100 displays the hemorrhage detection alert in the schedule screen on the monitor 150.

Figure 21:
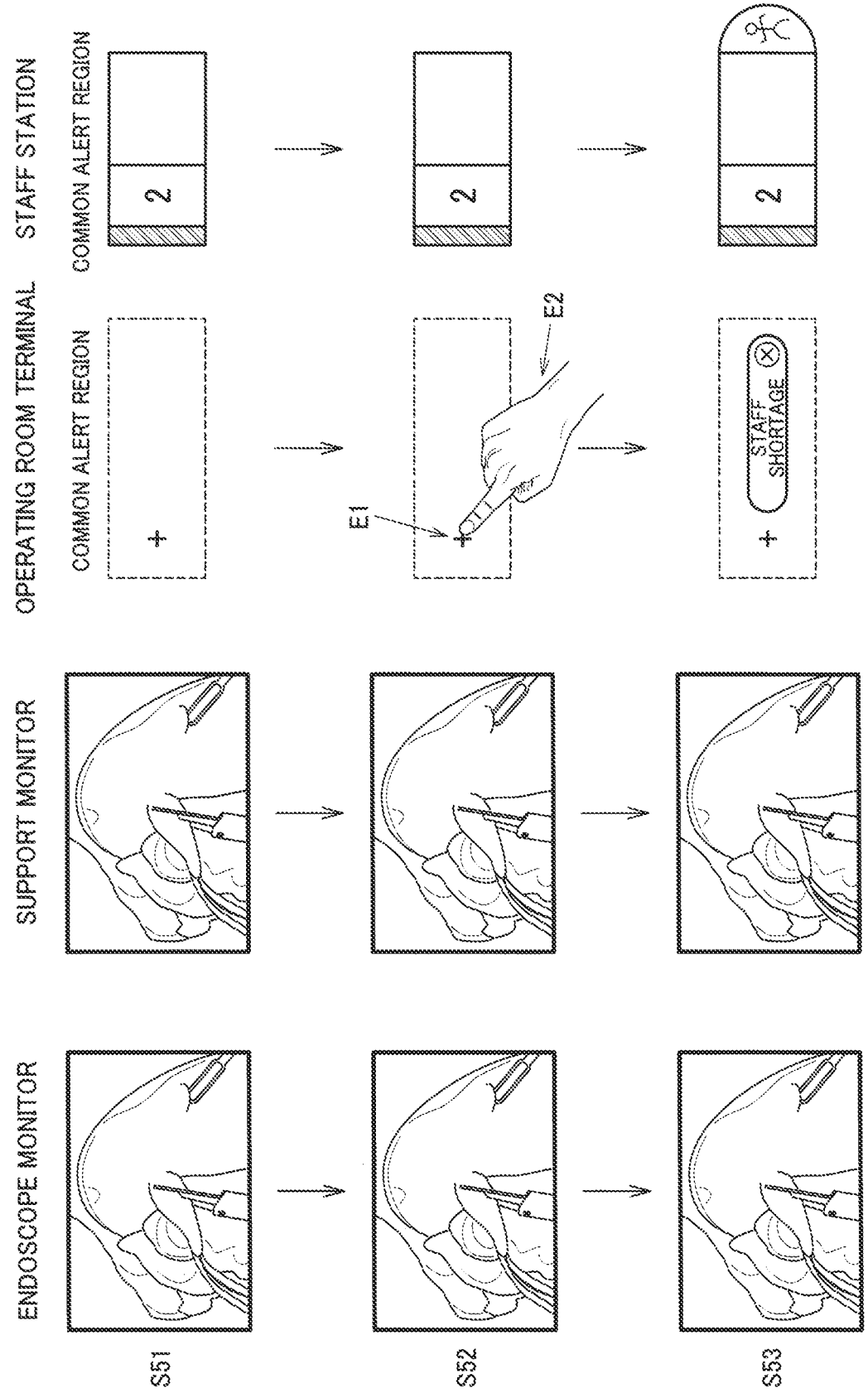
FIG. 21 is an example of display in the case of sharing a staff shortage alert.

FIG. 21 shows an example of display in the case of sharing a staff shortage alert. On the endoscope monitor 252, a live image of surgery is displayed as it is regardless of the result of hemorrhage detection. Since staff shortage is irrelevant to the image recognition process, the live image of the surgery is displayed as it is on the support monitor 251 regardless of whether or not there is staff shortage.

As shown in step S51, if the staff shortage alert is not input, the staff shortage alert is not displayed in the terminal in the operating room or the schedule screen in the staff station.

As shown in step S52, the staff shortage alert is input by a member when he/she recognizes staff shortage. As shown in E1, a "+" mark is displayed in the common alert region in the terminal. As shown in E2, when a member taps the "+" mark, a list of alerts that can be manually input is displayed. The member selects the staff shortage alert from the list.

As shown in step S53, when accepting a staff shortage alert that is manually input, the processor 211 of the operating room system 200 displays the staff shortage alert on the terminal in the operating room, and also notifies the staff station system 100 of information of the staff shortage alert. The processor 111 of the staff station system 100 displays the staff shortage alert in the schedule screen on the monitor 150.

Figure 22:
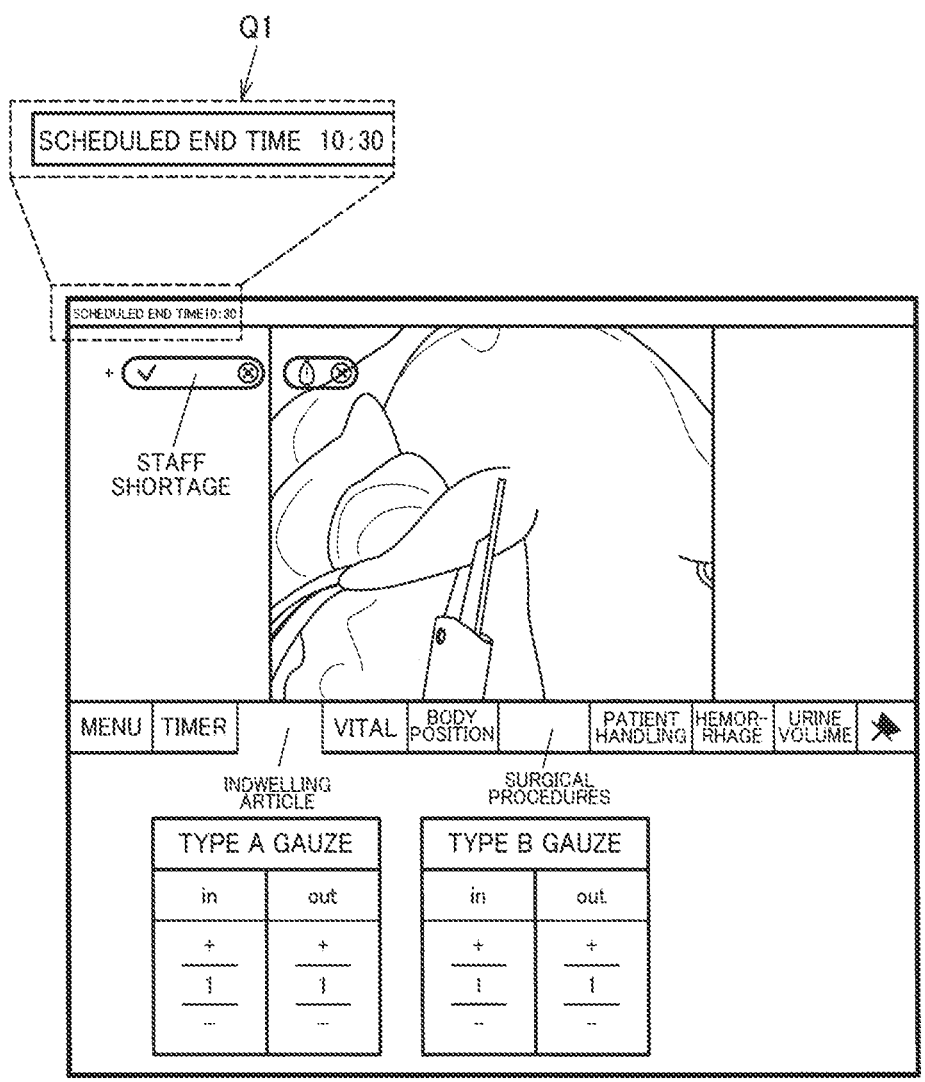
FIG. 22 is a diagram illustrating sharing information of surgery time between an operating room and a staff station.

FIG. 22 shows a diagram illustrating sharing of surgery time in the operating room and the staff station. As shown in Q1, a display region for surgery time information is provided in an upper portion of the screen of each terminal in the operating room. This display region displays a scheduled end time of the surgery.

Specifically, the processor 111 of the staff station system 100 transmits information of the scheduled end time to the operating room system 200 based on the information of the surgery time set in the surgery plan bar. The processor 211 of the operating room system 200 displays a scheduled end time on the first to third terminals 221-223 based on the received information. When the surgery is rescheduled and the scheduled end time is modified in the staff station, the processor 111 of the staff station system 100 transmits information of the modified scheduled end time to the operating room system 200. The processor 211 of the operating room system 200 displays the modified scheduled end time on the first to third terminals 221-223 based on the received information.

In the present embodiment described above, the processor 211 establishes communication connection with a staff station terminal 110 positioned in the staff station outside the operating room where the surgeon 294 performs a surgery. The processor 211 transmits the information of the common alert to the staff station terminal 110, thereby displaying an alert synchronized with the common alert on the monitor 150 of the staff station terminal 110.

According to the present embodiment, the common alert is shared between the operation team members in the operating room and the staff in the staff station. This makes it easier for operation team members in the operating room and the staff in the staff station to work together to conduct a surgery.

Further, in the present embodiment, when a predetermined surgery situation is detected based on the result of the image analysis on the live image, the processor 211 transmits information of a common alert regarding the predetermined surgery situation to the staff station terminal 110.

According to the present embodiment, the common alert can be automatically displayed on the terminal in the operating room and the monitor in the staff station based on the result of image analysis.

In the examples of FIGS. 19 and 20, the predetermined surgery situation corresponds to hemorrhage. However, the predetermined surgery situation may be any situation that can be detected by the image recognition process.

Further, in the present embodiment, when the processor 211 accepts an instruction input from a member via a terminal, the processor 211 may transmit information of a common alert regarding the instruction input to the staff station terminal 110.

According to the present embodiment, based on the state recognized by a member, the common alert regarding the state can be displayed on the terminal in the operating room and the monitor in the staff station.

In the examples of FIGS. 19 and 21, the instruction input corresponds to the input of the staff shortage alert. However, the instruction input may be any instruction input insofar as it relates to the state recognized by the member.

Further, in the present embodiment, the processor 211 transmits the information of the common alert to the staff station terminal 110 in association with the surgery performed by the surgeon 294, thereby causing the alert synchronized with the common alert to be displayed on the monitor 150 of the staff station terminal 110 in association with the surgery performed by the surgeon among the plurality of surgeries managed by the staff station terminal 110.

According to the present embodiment, the common alert associated with the surgery performed by the surgeon 294 is displayed on the monitor in the staff station. This enables the staff in the staff station outside the operating room to recognize which surgery the alert is generated for.

The processor 211 associates the surgery performed by the surgeon 294 with the information of the common alert by associating the operating room number with the information of the common alert. It may also be arranged such that the processor 211 associates the information of the common alert with information for identifying a surgery plan bar scheduled by the staff station system 100.

Further, in the present embodiment, the processor 211 receives a scheduled end time of the surgery from the staff station terminal 110 that manages the schedule of the surgery performed by the surgeon 294. The processor 211 performs processing of displaying the received scheduled end time in the display screen. When the scheduled end time is rescheduled in the staff station terminal 110, the processor 211 performs processing of displaying the rescheduled scheduled end time in the display screen.

According to the present embodiment, the surgery time information is shared between the operation team members in the operating room and the staff in the staff station. This makes it easier for operation team members in the operating room and the staff in the staff station to work together to conduct a surgery.

4. Third Detailed Configuration Example

A surgery generally cannot be completed by only a surgeon, but also includes planning, preparation, assistance, and the like, which are performed by a team of multiple members. The team members also include those outside the operating room. Medical service workers such as surgeons and nurses may perform multiple surgeries in a day; in addition, in hospitals, surgeries are often performed simultaneously in multiple operating rooms. For this reason, it is desirable for the surgical support system to provide information support so that the entire hospital can manage the surgery team and surgical equipment according to the progress of the surgery in each operating room or the resource status of personnel, equipment and the like.

The Japanese Unexamined Patent Application Publication No. JP2007-249251 described above discloses a clinical communication device and a hospital information system capable of linking an electronic medical record with event information of a patient or a doctor, thereby enabling information exchange. However, this previously-known technique relates to a schedule of a treatment plan (clinical path) for each patient, and is incapable of performing scheduling of surgeries in the entire hospital in light of a state of personnel, equipment, or the like.

The third detailed configuration example in light of such circumstances is described below.

Figure 23:
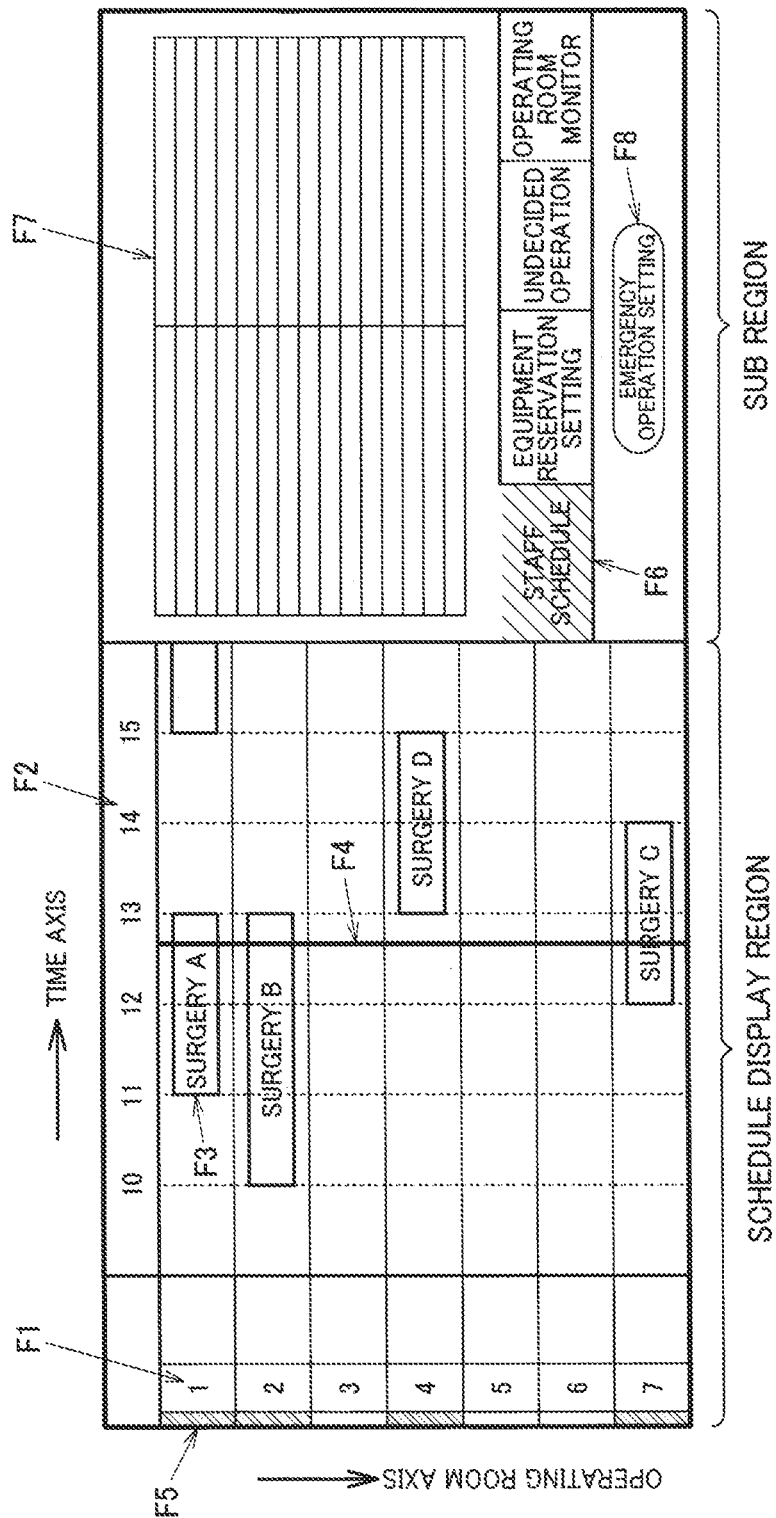
FIG. 23 is an example of schedule screen displayed on a monitor of a staff station system.

FIG. 23 shows an example of schedule screen displayed on the monitor 150 of the staff station system 100. The schedule screen includes a schedule display region in which a surgery schedule is displayed, and a sub region used for scheduling work or the like. For example, the schedule display region is positioned on the left side of the screen, and the sub region is displayed on the right side of the screen.

In the schedule display region, as shown in F1, the vertical axis corresponds to the operating room axis, and the operating room numbers are arranged along the vertical axis. The vertical axis is not limited to those showing numbers insofar as it represents operating room information for identifying each operating room. As shown in F2, the horizontal axis is a time axis. For example, the displayed time may be made slidable by a drag operation or the like. As shown in F3, a surgery plan bar indicating a scheduled surgery time of each surgery is displayed in the field of each operating room. FIG. 23 shows an example in which surgeries A to D are scheduled. As shown in F4, a vertical line showing the current time is displayed at a position corresponding to the current time on the time axis. In FIG. 23, the vertical line is a thick solid line; however, in the actual display, it is, for example, a blue solid line or the like. As shown in F5, on the left side of the operating room number, a sign indicating the state in the operating room is displayed. Examples of the state of the operating room include "completion of equipment installation", "completion of confirmation of installation", "surgery in progress", "vacant", "patient out", and the like. These signs are displayed when the state of the operating room is notified from the operating room. For example, when the start of the surgery is notified from the operating room, a sign indicating the start is displayed on the left side of the operating room number. In FIG. 23, the operating rooms 1, 2 and 7 notified the start of surgeries A, B and C, and the sign indicating the start is displayed on the left side of each of the operating rooms 1, 2 and 7. Further, the confirmation of equipment for the surgery D is notified from the operating room 4, and a sign indicating the confirmation is displayed on the left side of the operating room 4.

In the sub region, as shown in F6, a plurality of tabs are displayed side by side. The tabs are selectable by a tap operation or the like. As shown in F7, a display content corresponding to the selected tab is displayed above the tab. The staff schedule tab is a tab for displaying a resource list of medical service workers, and is used when a medical service worker is allocated to a surgery schedule. The equipment schedule setting tab is a tab for displaying a list of equipment resources, and is used when an equipment is allocated to a surgery schedule. The undecided operation tab is a tab for displaying a list of operations that are scheduled but the details thereof have not been decided. The operating room monitor tab is a tab for displaying a video from a camera installed in each operating room. FIG. 23 shows an example in which the staff schedule tab is selected. As shown in F8, an emergency operation setting button is displayed under the tab. When this button is tapped, an emergency operation setting screen for scheduling an emergency operation is displayed.

Details of the staff schedule tab, the equipment schedule setting tab, and the operating room monitor tab will be described later. The undecided operation tab has the following functions. The undecided operation tab shows a surgery for which date and start time have not been decided at the time of loading information from an electronic medical record or the like. Further, when the surgery of the surgery plan bar in the schedule screen is cancelled or postponed, the surgery plan bar is returned to the undecided operation tab. The undecided operation tab also provides a blank surgery plan bar for a new surgery. Further, the surgery plan bar in the undecided operation tab is deletable.

Figure 24:
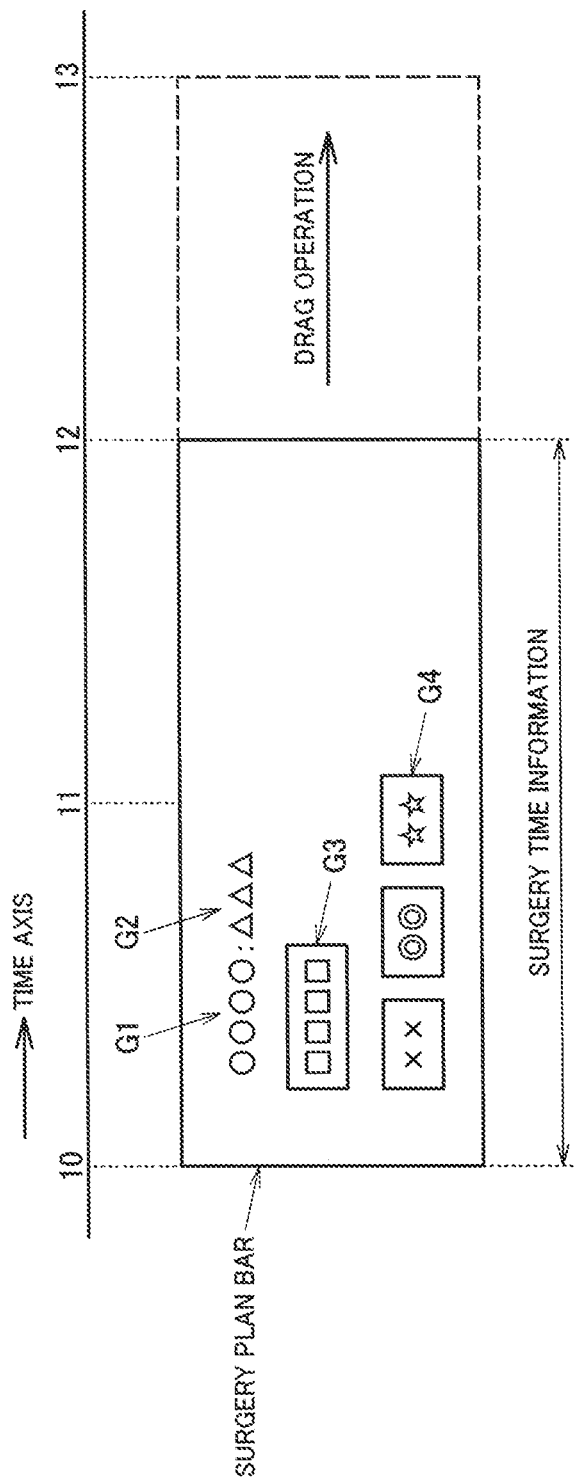
FIG. 24 is an example of surgery plan bar.

FIG. 24 shows an example of a surgery plan bar. On the schedule, a single surgery plan bar is displayed for a single surgery. In the surgery plan bar, patient information regarding the patient having the surgery, surgery time information regarding scheduled surgery time, surgery content information regarding the contents of surgery, and surgery resource information regarding the surgery resource allocated to the surgery are associated with each other.

The patient information includes, for example, information of the name, sex, weight, blood type, disease name, anamnesis, and the like of the patient. The staff station system 100 acquires patient information from an electronic medical record, input information from staff, or the like, and displays the patient information in association with the surgery plan bar. As shown in G1, among the patient information, the name of the patient is displayed in the surgery plan bar. Information that is not displayed in the surgery plan bar is also associated with the surgery plan bar and can be displayed on, for example, a detailed display screen or the like. The detailed display screen is displayed on the monitor 150 when, for example, the surgery plan bar is tapped.

The surgery time information includes information of scheduled surgery time indicating the scheduled start time and end time of the surgery. The scheduled surgery time may be indicated by, for example, a scheduled start time and a scheduled end time of the surgery, or by a scheduled start time of the surgery and a length of time required for the surgery. The position and the length of the surgery plan bar on the time axis are set based on the surgery time information. More specifically, the left side of the surgery plan bar indicates the scheduled start time, the right side thereof indicates the scheduled end time, and the length of the bar indicates the length of time required for the surgery.

The surgery content information includes, for example, information of operative method, surgical procedures, and the like. As shown in G2, among the surgery content information, the operative method is displayed in the surgery plan bar. Information that is not displayed in the surgery plan bar is also associated with the surgery plan bar and can be displayed on, for example, a detailed display screen or the like.

The surgery resource information includes, for example, information of the operating room, medical service worker, equipment, and the like. The medical service workers are the operation team members, including a surgeon, an anesthesiologist, and nurses in charge of the surgery. The position of the surgery plan bar on the surgery axis is set based on the information of operating room among the resource information. For example, when the operating room No. 2 is allocated, a surgery plan bar is displayed in the field of the operating room No. 2 in the surgery schedule. In addition, as shown in G3 and G4, among the surgery resource information, an anesthesiologist and nurses are displayed in the surgery plan bar. G3 is an anesthesiologist and G4 are nurses. Information that is not displayed in the surgery plan bar is also associated with the surgery plan bar and can be displayed on, for example, a detailed display screen or the like.

The storage device 112 of the staff station system 100 stores schedule information including the above-described various types of information, above-described information items associated with the surgery plan bar, and the like. The processor 111 displays a schedule screen on the monitor 150 based on the schedule information stored in the storage device 112. The processor 111 updates the schedule information stored in the storage device 112 based on a schedule input operation by the user.

The right side of the surgery plan bar, i.e., the scheduled end time, can be changed by a drag operation. FIG. 24 shows an example in which the scheduled end time is changed from 12:00 to 13:00.

Figure 25:
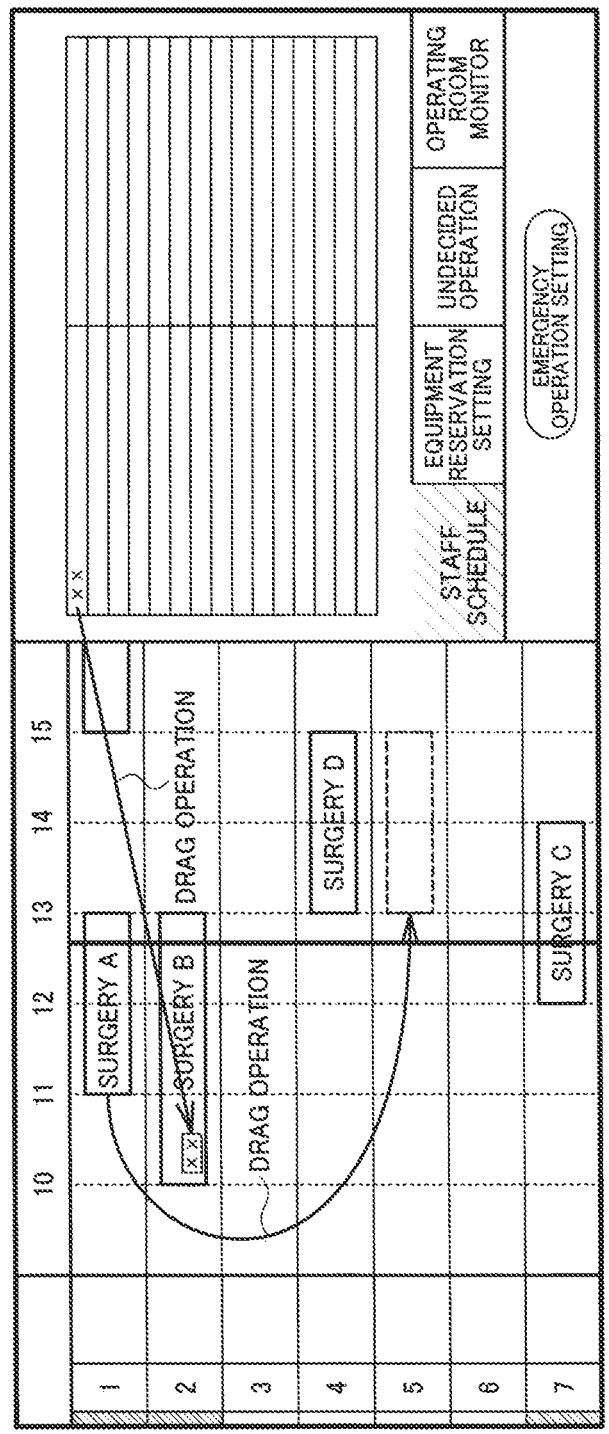
FIG. 25 is an example of drag operation during a scheduling work.

As shown in FIG. 25, the position of the surgery plan bar on the time axis and that on the surgery axis can be changed by a drag operation. FIG. 25 shows an example in which the operating room No. 1 of the surgery plan bar of surgery A is changed to the operating room No. 5, and the scheduled surgery time of 11:00 to 13:00 is changed to a scheduled surgery time of 13:00 to 15:00. Such an operation to move the surgery plan bar or change the scheduled end time is limited so as to avoid double scheduling of a plurality of surgeries at the same time or in the same operating room. It may also be arranged such that the time interval between the scheduled surgery time of the surgery plan bar to be moved and the scheduled surgery time of another surgery plan bar already shown in the target operating room must be no less than the minimum time required for preparation, surgery, or cleanup.

Also, as shown in FIG. 25, a medical service worker can be allocated to the surgery plan bar from the medical service worker list by a drag operation. Similarly, an equipment can be allocated to the surgery plan bar from the equipment list by a drag operation. FIG. 25 illustrates an example in which the medical service worker XX displayed in the medical service worker list is dragged to the surgery plan bar of surgery B, thus assigning the medical service worker XX to the surgery B.

The surgical support system 50 of the present embodiment described above includes the processor 111 and the storage device 112. The processor 111 performs processing of displaying on the monitor 150 a surgery schedule screen indicating the surgery schedule. The storage device 112 stores surgery time information regarding scheduled surgery time, surgery content information regarding the contents of surgery, and surgery resource information regarding surgery resource(s) that can be allocated to each surgery, which are used to create a surgery schedule. The processor 111 performs processing of displaying on the monitor 150 a surgery schedule screen displaying surgery time information and surgery content information with regard to the surgery on the surgery schedule, as well as surgery resource information regarding surgery resources allocated to the surgery.

According to the present embodiment, with the surgery schedule screen displayed on the monitor in the staff station, it is possible to present the surgery schedule screen to the staff of the hospitals including the team members outside the operating room. This enables information support that allows the entire hospital to manage the surgery team and surgical equipment according to the resource status of personnel, equipment, and the like.

Further, in the present embodiment, the surgery resource information includes at least one of operating room information regarding operating room that can be allocated to each surgery, medical service worker information regarding medical service worker that can be allocated to each surgery, or equipment information regarding equipment that can be allocated to each surgery.

According to the present embodiment, a surgery schedule screen in which at least one of the operating room information, the medical service worker information, or the equipment information is allocated to the surgery as surgery resource information can be provided to the staff of the hospital including the team members outside the operating room.

Further, in the present embodiment, the surgery content information includes at least one of operative method information regarding operative method or patient information regarding patient.

According to the present embodiment, a surgery schedule screen in which at least one of the operative method information or the patient information is allocated to the surgery as the surgery content information can be provided to the staff of the hospital including the team members outside the operating room.

Further, in the present embodiment, the surgery resource information includes operating room information regarding operating room that can be allocated to each surgery. The schedule screen has a surgery plan bar. The surgery plan bar is provided on a matrix including an operating room axis and a time axis, showing an operating room, a scheduled surgery time, and a surgery content.

According to the present embodiment, by providing the surgery plan bar on the matrix, it is possible to plan the operating room and the scheduled surgery time for the surgery. Further, by viewing the surgery plan bar on the matrix, the operating room, the scheduled surgery time, and the surgery content of the surgery can be clearly understood.

Further, in the present embodiment, the surgery plan bar is provided, on the operating room axis on the matrix, in a position corresponding to the operating room where the surgery indicated by the surgery plan bar is performed. Furthermore, the surgery plan bar is displayed on the time axis on the matrix as a bar having the start time and the end time of the surgery indicated by the surgery plan bar at the both ends.

According to the present embodiment, the surgery and the scheduled surgery time can be planned by determining, on the matrix, the position of the surgery plan bar on the surgery axis, as well as both ends or the length thereof on the time axis. Further, by viewing the position on the surgery axis of the surgery plan bar planned on the matrix, as well as the both ends or the length thereof on the time axis, the operating room and the scheduled surgery time of the surgery can be clearly recognized.

Further, in the present embodiment, when accepting a drag operation for moving the position of the surgery plan bar on the matrix, the processor 111 performs processing of moving the surgery plan bar to a position corresponding to at least one of an operating room different from the operating room before the movement or a scheduled surgery time different from the scheduled surgery time before the movement. The drag operation is, for example, a drag operation using the touch panel of the monitor 150.

According to the present embodiment, it is possible to reschedule the surgery in a visually and intuitively understandable manner by a drag operation on the matrix. Further, the scheduled surgery time can be changed by a drag operation in the time-axis-wise direction on the matrix, and the operating room can be changed by a drag operation in the surgery-axis-wise direction.

Further, in the present embodiment, when accepting a drag operation for changing the end time indicated by the surgery plan bar on the matrix, the processor 111 performs processing of displaying on the monitor 150 the surgery plan bar the end time of which is changed based on the drag operation.

According to the present embodiment, it is possible to reschedule the end time of the surgery in a visually and intuitively understandable manner by a drag operation on the matrix.

Further, in the present embodiment, the processor 111 performs processing of displaying on the monitor 150 a resource list of surgery resources together with the schedule screen.

According to the present embodiment, it is possible to present the resource list of the surgery resources together with the schedule screen to the staff of the hospital including the team members outside the operating room. Accordingly, the staff can understand the surgery resources that can be allocated to each surgery.

Further, in the present embodiment, when accepting a drag operation for moving a resource included in the resource list to the surgery plan bar, the processor 111 performs processing of allocating the moved resource to the surgery plan bar and displaying the resource on the monitor 150.

According to the present embodiment, it is possible to allocate a resource to the surgery in a visually and intuitively understandable manner by a drag operation from the resource list to the surgery plan bar.

The present embodiment may be performed as a surgical support method as described below. The surgical support method may be performed as a method of operating the surgical support system 50. The surgical support method includes storing surgery time information regarding scheduled surgery time, surgery content information regarding the contents of surgery, and surgery resource information regarding surgery resource(s) that can be allocated to each surgery, which are used to create a surgery schedule. In addition, the surgical support method includes performing processing of displaying on the monitor 150 a surgery schedule screen displaying surgery time information and surgery content information with regard to the surgery on the surgery schedule, as well as surgery resource information regarding surgery resources allocated to the surgery.

Moreover, the present embodiment may be implemented as a program or a computer-readable non-transitory information storage medium, as described below. The program causes a computer to execute storing surgery time information regarding scheduled surgery time, surgery content information regarding the contents of surgery, and surgery resource information regarding surgery resource(s) that can be allocated to each surgery, which are used to create a surgery schedule. In addition, the surgical support method causes a computer to execute processing of displaying on the monitor 150 a surgery schedule screen displaying surgery time information and surgery content information with regard to the surgery on the surgery schedule, as well as surgery resource information regarding surgery resources allocated to the surgery. The information storage medium stores the program. The computer reads out the program from the information storage medium and executes the program, thereby realizing the functions of the surgical support system 50. The information storage medium can be implemented by, for example, an optical disc, a memory card, an HDD, a semiconductor memory, or the like. The semiconductor memory is, for example, a ROM or a non-volatile memory.

Figures 26, 27:
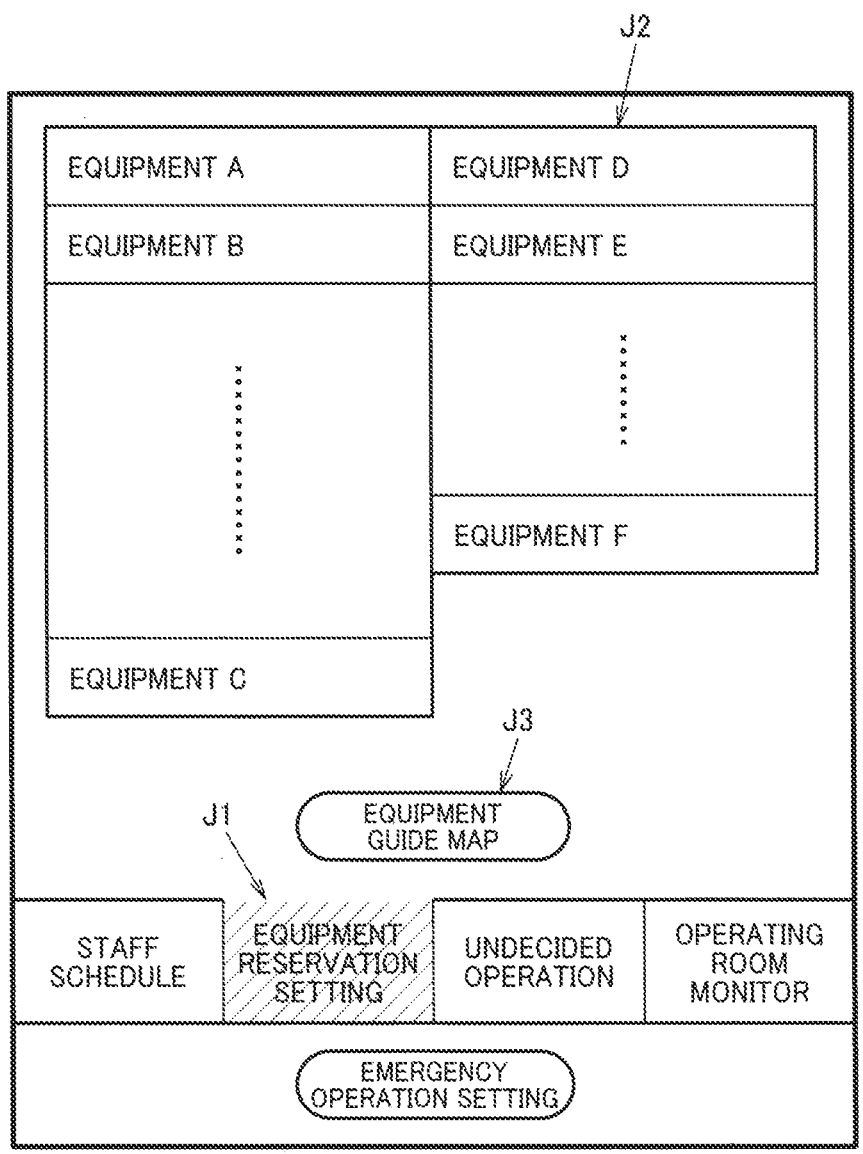
FIG. 26 is an example of display of a medical service worker list.
FIG. 27 is an example of display of a sub region when an equipment reservation setting tab is selected.

FIG. 26 shows an example of display of a medical service worker list. As shown in H1, each field of the list displays the name of a staff member who can be allocated to the surgery. When the staff member in the list is selected, the surgery plan bar to which he/she has been assigned is highlighted. Examples of highlights include adding a frame of a predetermined color to the surgery plan bar, and displaying a predetermined mark in the surgery plan bar. Also in the case where the resource is equipment, similarly, when the equipment in the list is selected, the surgery plan bar to which the equipment is allocated is highlighted.

As shown in H2 and H3, icons are displayed on the right side of each field of the medical service worker list. H2 is a number icon, and H3 is a mark icon. The number icons 1, 2 and 3 are switchable by a tap operation. The mark icon is switchable between a circle mark, a triangle mark and an X mark by a tap operation. Each icon represents any arbitrary item. For example, the number icon may represent working schedule of staff, and a mark icon may represent staff status, such as during work or breaks.

FIG. 27 shows an example of display of the sub region when an equipment reservation setting tab is selected. When the equipment reservation setting tab is selected as shown in J1, a list of equipment resources is displayed above the tab as shown in J2. In each field of the list, the name of equipment that can be allocated to the surgery is displayed. When an equipment in the list is selected, the surgery plan bar to which the equipment is allocated is highlighted. Examples of highlights include adding a frame of a predetermined color to the surgery plan bar, and displaying a predetermined mark in the surgery plan bar. As shown in J3, an equipment guide map button is displayed below the list of equipment resources. When this button is pressed by a tap operation or the like, an equipment guide map is displayed in the schedule screen. The equipment guide map is described later in FIG. 29.

In the present embodiment described above, when accepting an operation of selecting a resource from a resource list, the processor 111 performs processing of highlighting the surgery plan bar to which the selected resource is allocated.

According to the present embodiment, it is possible to visually and intuitively recognize whether or not the desired resource has already been reserved for another surgery on the schedule matrix. Alternatively, it is possible to visually and intuitively recognize which surgery uses the resource that has been checked for its reservation status on the schedule matrix.

Figure 28:
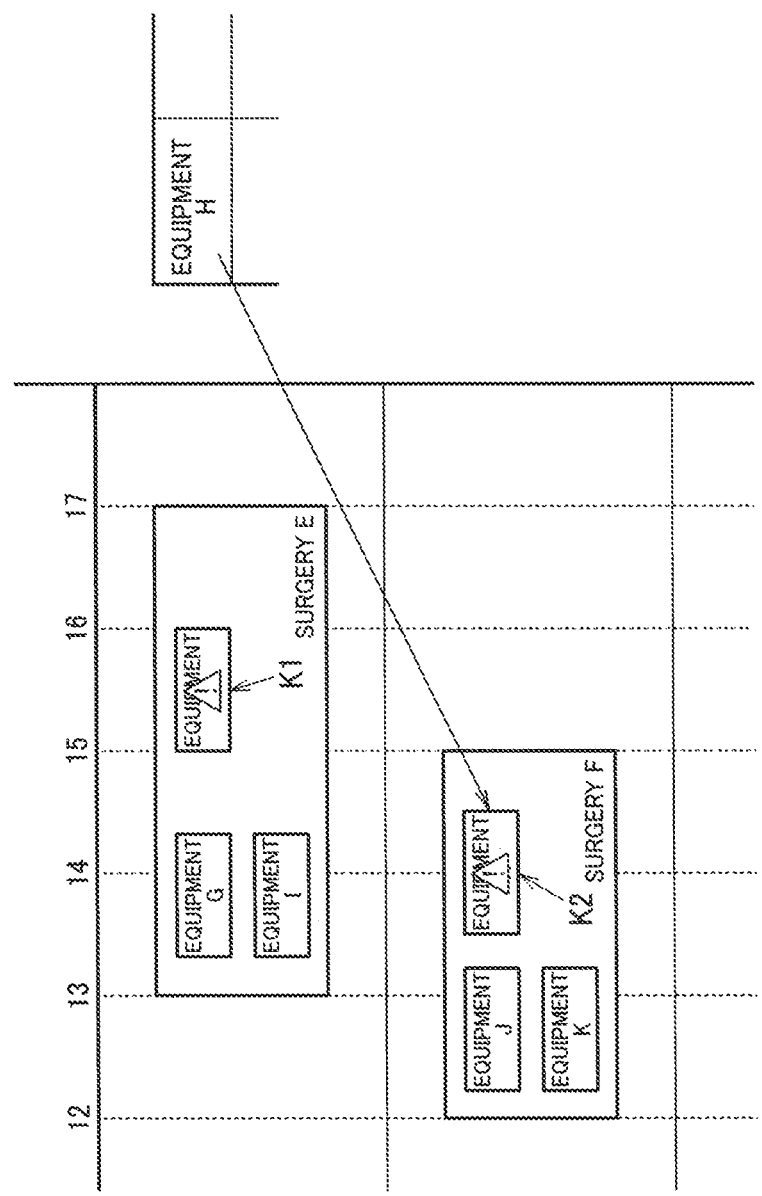
FIG. 28 is an example of alert display for resource double allocation.

FIG. 28 shows an example of alert display for double allocation of resources. This case assumes that the scheduled surgery time of surgery E and the scheduled surgery time of surgery F overlap during 13:00 to 15:00 and that the equipment H has already been allocated to the surgery plan bar of the surgery E, as shown in K1. Then, as shown in K2, if the equipment H is allocated to the surgery plan bar of the surgery F by dragging it from the list of equipment resources, an alert is displayed on the name of the equipment H in both the surgery plan bar for the surgery E and the surgery plan bar for the surgery F. FIG. 28 shows an example in which an exclamation mark is displayed on the name of the equipment H. The alert may also be displayed such that the name of the equipment H is, for example, colored or hatched. Similarly, when the resource is a medical service worker, in the case of double reservation, an alert is displayed on the name of the staff member in the surgery plan bar. When the allocation results in double reservation of the resource, it is also possible to disable the allocation of the resource instead of displaying an alert as described above. The determination of double reservation may be made by considering not only the scheduled surgery time but also the time required for preparation, such as sterilization.

In the present embodiment described above, the processor 111 performs processing of displaying on the monitor 150 an alert for warning double resource allocation when the resource that has been allocated to a surgery plan bar by a drag operation is a resource already allocated to another surgery plan bar that overlaps in scheduled surgery time with the target surgery plan bar.

According to the present embodiment, it is possible to present an alert to staff when the same resource is reserved for two or more surgery plan bars with overlapping scheduled surgery time. Such a visual and intuitive recognition of double resource reservation will reduce the burden of scheduling work.

Figure 29:
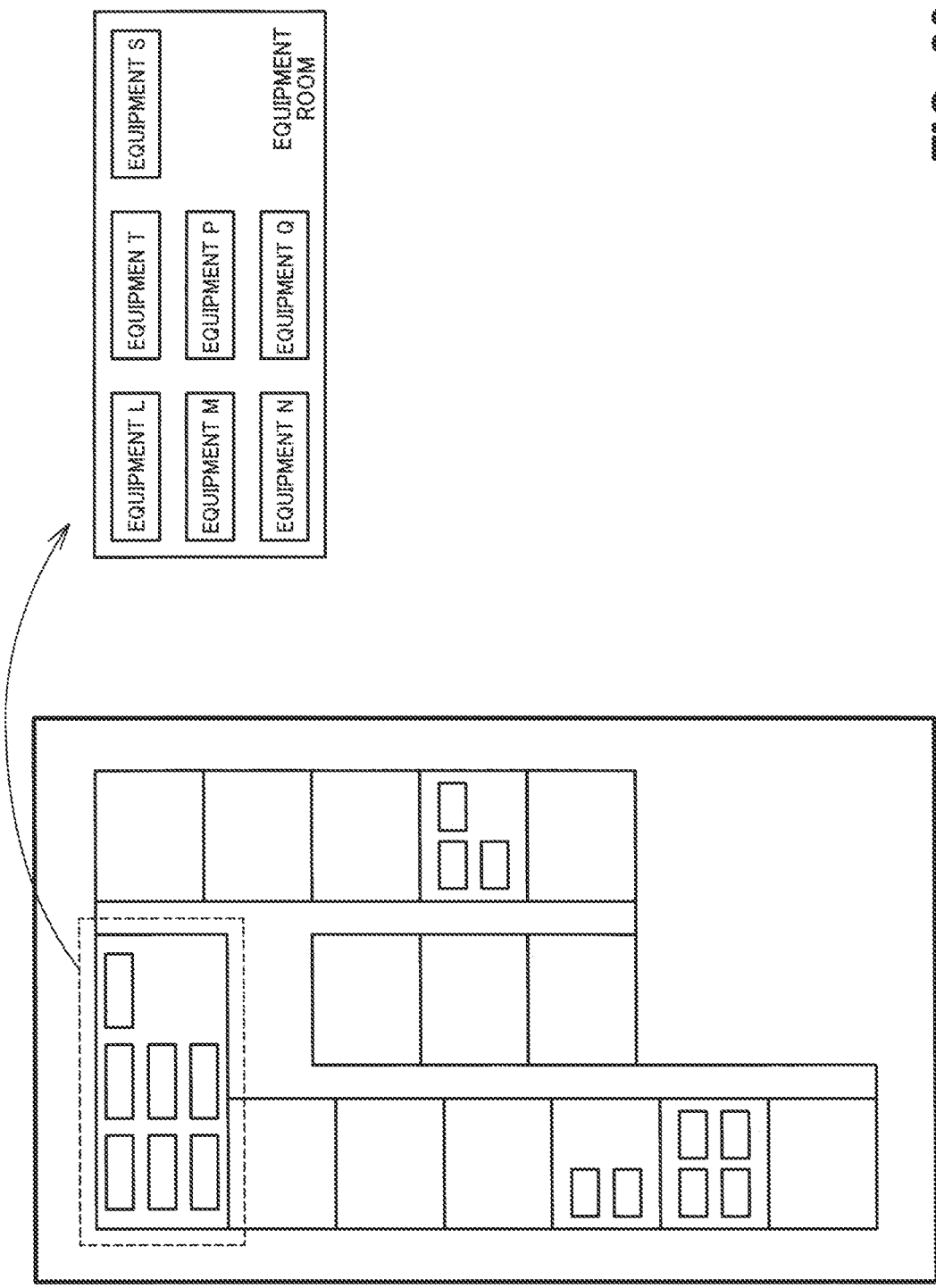
FIG. 29 is an example of equipment guide map.

FIG. 29 shows an example of equipment guide map. As shown in the left figure, the equipment guide map displays a floor map of the facility where the surgical support system 50 is used, and the location of each piece of equipment is displayed in the floor map. Specifically, as shown in the right figure, each room in the floor map displays the name of the room and the names of equipment in the room. When a surgery plan bar in the schedule screen is selected, the equipment allocated to the surgery plan bar may be highlighted in the equipment guide map.

The location of equipment is determined, for example, as follows. A beacon tag is attached to each piece of equipment, and receivers for receiving beacon signals transmitted from the beacon tags are installed in the facility. The processor 111 of the staff station system 100 specifies the location of each piece of equipment based on the beacon signals received by the receivers. It may also be arranged such that the place for storing each piece of equipment is previously determined, and that the processor 111 specifies the location of equipment based on information of storage place and information of association between the surgery plan bar and the equipment. When a surgery associated with equipment is performed, the processor 111 determines that the equipment is in the operating room. Otherwise, the processor 111 determines that the equipment is stored in the storage place.

Further, in the present embodiment, the processor 111 performs processing of displaying on a monitor 150 a map screen showing locations of surgery resources.

According to the present embodiment, the map screen enables visual and intuitive recognition of the location of each resource in the facility. For example, in the preparation of surgery resources, the staff members will know where to go to obtain the resources.

Further, in the present embodiment, the processor 111 also acquires information of the locations of surgery resources in the facility where the surgical support system 50 is used, and, based on the acquired location information, performs processing of displaying the map screen showing the locations of surgery resources in the facility on the monitor 150.

According to the present embodiment, since the locations of the resources in the facility can be recognized from the acquired location information, it is possible to automatically generate a map screen showing the locations of resources.

5. Fourth Detailed Configuration Example

A surgery generally cannot be completed by only a surgeon, but also includes planning, preparation, assistance, and the like, which are performed by a team of multiple members. The team members also include those outside the operating room. Medical service workers such as surgeons and nurses may perform multiple surgeries in a day; in addition, in hospitals, surgeries are often performed simultaneously in multiple operating rooms. For this reason, it is desirable for the surgical support system to provide information support so that the entire hospital can manage the surgery team and surgical equipment according to the progress of the surgery in each operating room or the resource status of personnel, equipment and the like.

The Japanese Unexamined Patent Application Publication No. JP2007-249251 described above discloses a clinical communication device and a hospital information system capable of linking an electronic medical record with event information of a patient or a doctor, thereby enabling information exchange. However, this previously-known technique relates to a schedule of a treatment plan (clinical path) for each patient, and is incapable of performing scheduling of surgeries in the entire hospital in light of progress status of surgery in each operating room.

The fourth detailed configuration example in light of such circumstances is described below.

Figure 30:
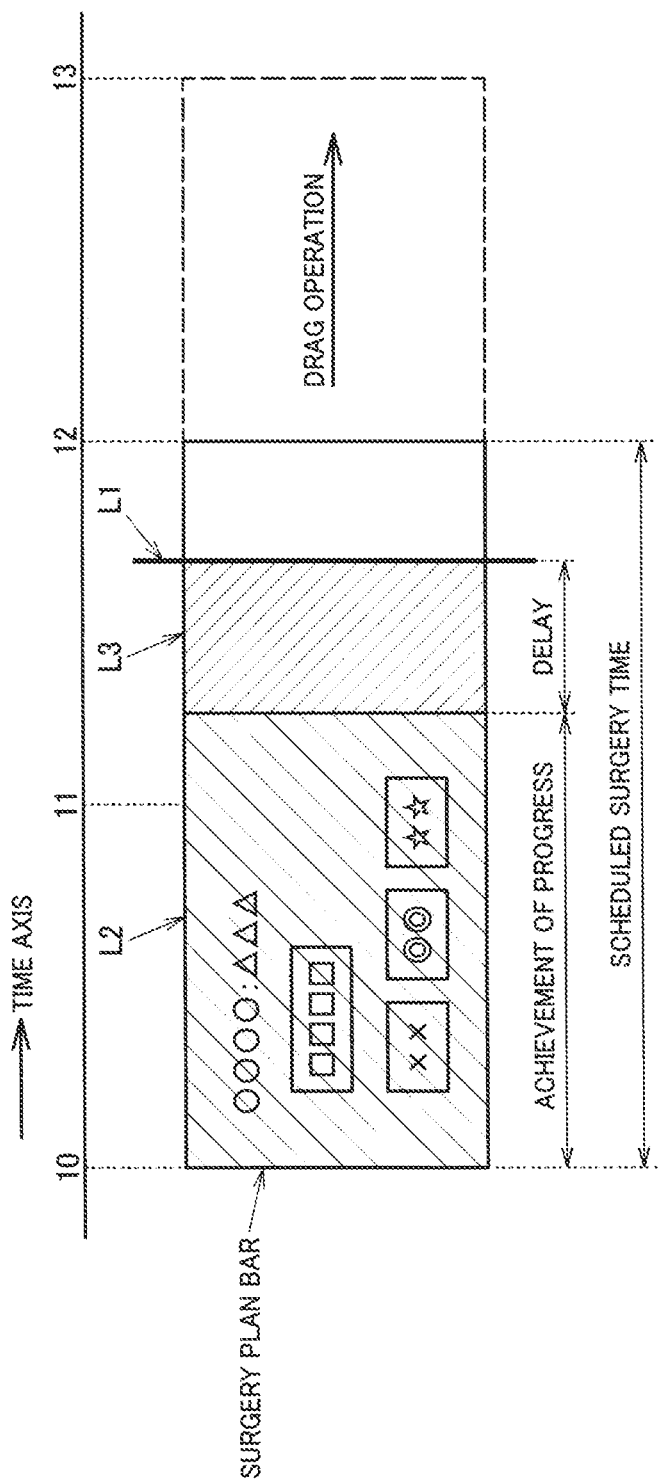
FIG. 30 is an example of display of a surgery progress status.

FIG. 30 shows an example of display of a surgery progress status. As shown in L1, a vertical line showing the current time is displayed in the surgery schedule screen. As shown in L2, the surgery plan bar has a progress achievement bar showing the achievement of progress of the surgery. The left side of the progress achievement bar indicates the surgery start time, and the length of the bar corresponds to the achievement of progress. As shown in L3, the surgery plan bar has a delay bar indicating a progress delay relative to the current time. The delay bar is displayed between the right edge of the progress achievement bar and the vertical line showing the current time. If the achievement of progress is ahead of the current time, the delay bar is not displayed and only the progress achievement bar is displayed. In this state, the right edge of the progress achievement bar extends to the right beyond the vertical line showing the current time.

The length of the progress achievement bar indicates the cumulative time of, for example, the manipulation steps completed. The processor 211 of the operating room system 200 determines the manipulation step based on the results of the image recognition process with respect to the live image or a manual input from an operation team member and transmits the information to the staff station system 100. The storage device 112 of the staff station system 100 stores in advance the time required for each manipulation step of the operative method used for the surgery. The processor 111 of the staff station system 100 reads out the time required for each manipulation step from the storage device 112, calculates the cumulative time of the manipulation steps completed, and displays a progress achievement bar in the surgery plan bar based on the cumulative time.

The staff in the staff station can change the scheduled end time by viewing the progress status displayed in the surgery plan bar and, as necessary, dragging the right edge of the surgery plan bar.

The surgical support system 50 of the present embodiment described above includes the processor 111 and the storage device 112. The processor 111 performs processing of displaying on the monitor 150 a surgery schedule screen indicating the surgery schedule. The storage device 112 stores surgery content information regarding the contents of the surgery, operating room information regarding the operating room, and surgery time information regarding the scheduled surgery time in association with the surgery on the surgery schedule. The processor 111 receives real-time surgery information, which is real-time information of a surgery state, from the operating room. The processor 111 performs processing of displaying on the monitor 150 a surgery schedule screen in which the surgery on the surgery schedule is associated with the real-time surgery information.

According to the present embodiment, the real-time surgery information, which is information regarding a real-time surgery state obtained from the operating room, is displayed in the surgery schedule screen in association with the surgery, thereby allowing the operation team members in the operating room and the staff in the staff station to share the real-time surgery state. This enables information support that allows the entire hospital to manage the surgery team and surgical equipment in light of the real-time surgery state in each operating room.

In FIG. 30, the real-time surgery information corresponds to the achievement of progress of surgery or the progress delay relative to the current time. However, the real-time surgery information is not limited to them and may also be, for example, an alert synchronized with the common alert of the operating room, which will be described later, or a real-time surgery video of the operating room, and the like.

Further, in the present embodiment, the real-time surgery information may be information regarding the progress of surgery acquired based on the results of image analysis on the live image of the surgery being conducted in the operating room.

Further, in the present embodiment, the surgery schedule screen has a progress display region, which shows the difference in achievement of progress with respect to the scheduled surgery time in association with the surgery by indicating the difference by a length of the bar.

The present embodiment enables information support that allows the entire hospital to manage the surgery team and surgical equipment in light of the progress status of the surgery in each operating room.

The live image may be any image insofar as it provides the information of surgery progress by image analysis. Examples include an endoscopic image captured by the endoscope system 270. In the example of FIG. 30, the information regarding the surgery progress is a progress achievement bar or a delay bar. However, the method of presenting information regarding the progress is not limited to them. In the example of FIG. 30, the progress display region corresponds to the delay bar. However, the method of indicating the difference in achievement of progress with respect to the scheduled surgery time by the length of the bar is not limited to the delay bar. The delay bar indicates a progress delay relative to the current time, which is to indicate a progress delay of the surgery schedule that is supposed to be completed by the current time. This difference in achievement of progress with respect to the scheduled surgery time is expressed by the length of the bar.

Further, in the present embodiment, the surgery time information also includes information of scheduled duration required for the surgery. The processor 111 displays the scheduled surgery duration in the surgery schedule screen in association with the surgery. When the processor 111 accepts an operation of changing the scheduled surgery duration, the processor 111 performs processing of displaying on the monitor 150 the surgery schedule screen the scheduled surgery duration of which has been changed based on the operation.

According to the present embodiment, the scheduled duration required for the surgery can be rescheduled according to the progress status of the surgery displayed in the surgery schedule screen. This makes it possible to visually and intuitively recognize the real-time progress status, and perform reschedule of surgery accordingly on the surgery schedule screen.

In FIG. 30, the operation of changing the scheduled surgery duration corresponds to the operation of dragging the right edge of the surgery plan bar. The length of the surgery plan bar indicates the scheduled surgery duration. Changing the surgery end time changes the scheduled surgery duration.

Further, in the present embodiment, the surgery schedule screen has a surgery plan bar. The surgery plan bar is provided on a matrix including an operating room axis and a time axis, showing an operating room, a scheduled surgery time, and a surgery content. The surgery plan bar is provided, on the operating room axis on the matrix, in a position corresponding to the operating room where the surgery indicated by the surgery plan bar is performed. The surgery plan bar is displayed on the time axis on the matrix as a bar having the start time and the end time of the surgery indicated by the surgery plan bar at the both ends. The progress display region indicates the difference in achievement of progress with respect to the scheduled surgery time as the length of the bar in the time axis in the surgery plan bar.

According to the present embodiment, the surgery schedule can be visually and intuitively recognized by viewing the surgery plan bar showing the operating room and the scheduled surgery time on the matrix. Moreover, since the progress display region is displayed in the surgery plan bar, it is possible to visually and intuitively recognize the progress relative to the scheduled surgery time planned in the surgery plan bar.

Further, in the present embodiment, when accepting a drag operation for extending the end time indicated by the surgery plan bar on the matrix, the processor 111 performs processing of displaying on the monitor 150 the surgery plan bar the end time of which is changed based on the drag operation.

According to the present embodiment, the scheduled duration required for the surgery can be rescheduled in a visually and intuitively understandable manner by performing a drag operation to extend the end time according to the progress status of the surgery displayed in the surgery plan bar.

The present embodiment may also be performed as a surgical support method as described below. The surgical support method may be performed as a method of operating the surgical support system 50. The surgical support method includes storing surgery content information regarding the contents of the surgery, operating room information regarding the operating room, and surgery time information regarding the scheduled surgery time in association with the surgery on the surgery schedule. The surgical support method also includes receiving real-time surgery information, which is real-time information regarding the surgery state, from the operating room. Moreover, the surgical support method includes performing processing of displaying on the monitor 150 the surgery schedule screen indicating a surgery schedule in which the surgery on the surgery schedule is associated with the real-time surgery information.

Moreover, the present embodiment may be implemented as a program or a computer-readable non-transitory information storage medium, as described below. The program causes a computer to execute storing surgery content information regarding the contents of the surgery, operating room information regarding the operating room, and surgery time information regarding the scheduled surgery time in association with the surgery on the surgery schedule. Also, the surgical support method causes a computer to execute receiving real-time surgery information, which is real-time information regarding the surgery state, from the operating room. Also, the surgical support method causes a computer to execute processing of displaying on the monitor 150 the surgery schedule screen indicating a surgery schedule in which the surgery on the surgery schedule is associated with the real-time surgery information.

Figure 31:
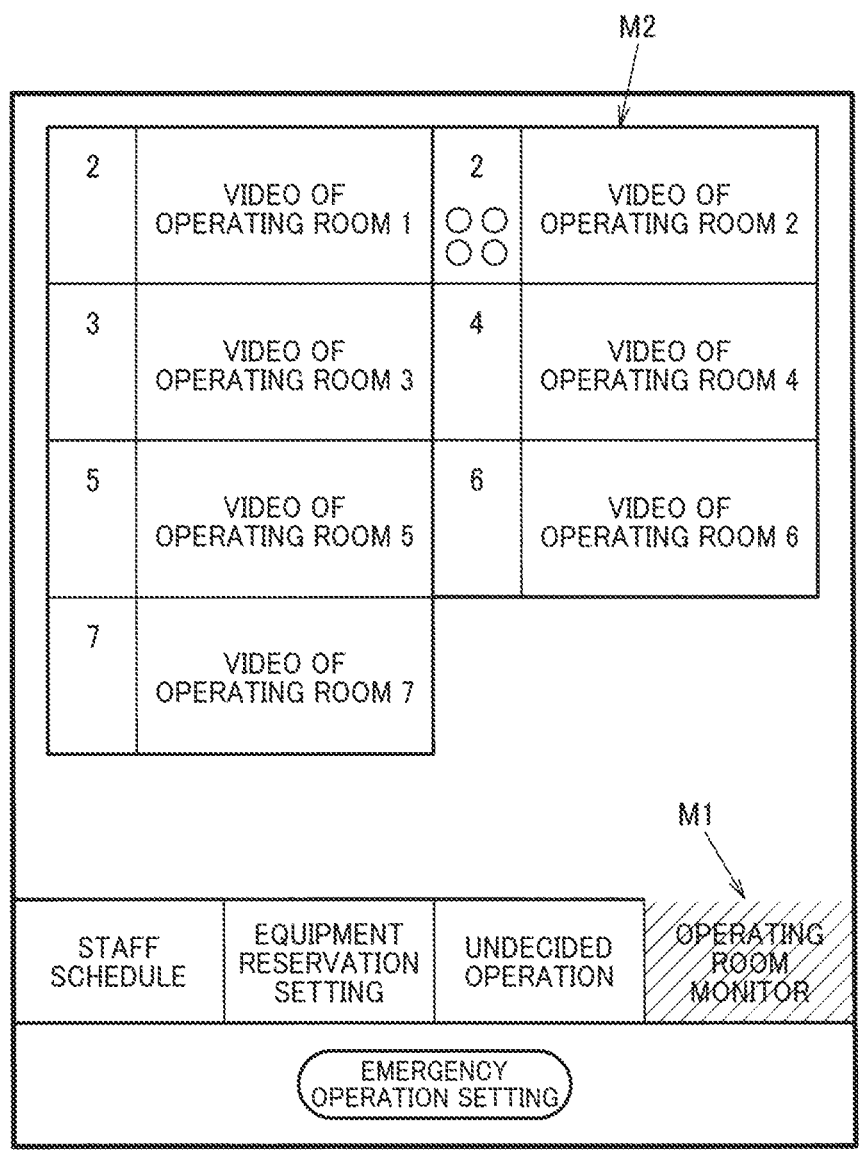
FIG. 31 is an example of display of a sub region when an operating room monitor tab is selected.

FIG. 31 shows an example of display of a sub region when an operating room monitor tab is selected. When the operating room monitor tab is selected as shown in M1, a list of real-time video for each operating room is displayed above the tab, as shown in M2. A single field of the list displays a real-time video of a single operating room. FIG. 31 shows an example in which there are seven operating rooms and real-time videos of the seven operating rooms are displayed. The real-time video of an operating room is a video taken by a camera installed in the operating room, which is, for example, a video showing a bird's-eye view of the operating room. When a surgery is performed in the operating room, the real-time video is a real-time surgery video showing the real-time state of the surgery.

Figure 32:
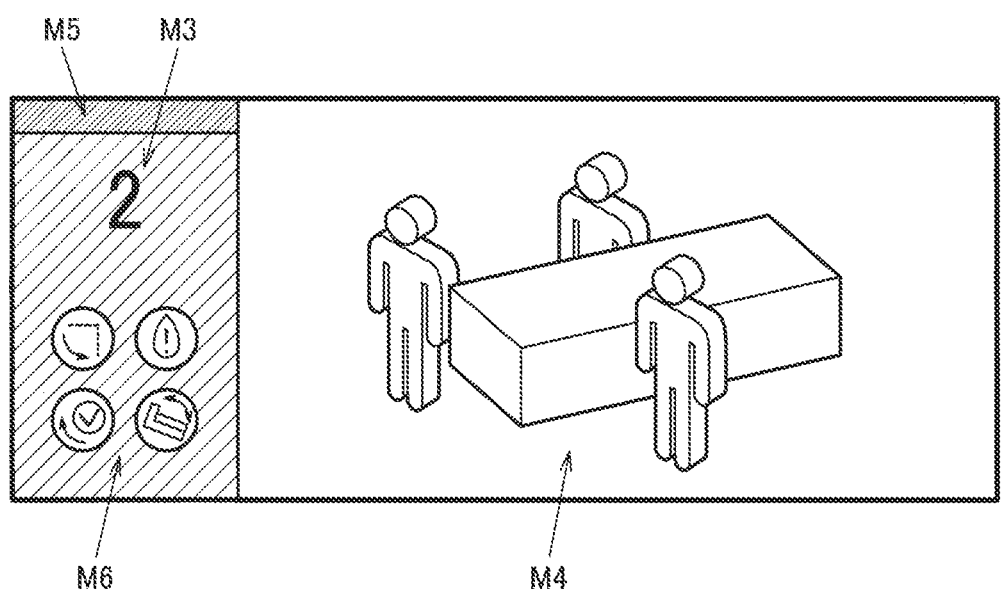
FIG. 32 is an example of real-time video display with regard to an operating room in a real-time video list.

FIG. 32 shows an example of real-time video display for an operating room in the real-time video list. As shown in M3, the operating room number is displayed on the left side of the field. As shown in M4, a real-time video of the operating room is displayed on the right side of the field. As shown in M5, a sign indicating that a surgery is being performed in the operating room is displayed above the operating room number. As shown in M6, an alert synchronized with the common alert displayed in the terminal of the operating room is displayed below the operating room number.

The processor 111 of the staff station system 100 associates the real-time surgery video for each operating room with the surgery, and accumulates it in the storage device 112. The accumulated real-time surgery videos can be reproduced as past surgery videos. More specifically, when the processor 111 accepts an operation of reproducing a past video of a surgery, the processor 111 performs processing of reading out the past surgery video associated with the surgery from the storage device 112 and displaying it on the monitor 150.

In the present embodiment described above, the real-time surgery information includes the real-time surgery video of the surgery being conducted in the operating room. The processor 111 performs processing of displaying on the monitor 150 a real-time surgery video in association with the operating room where the surgery is conducted.

According to the present embodiment, the real-time surgery video is displayed in the monitor in association with the operating room, thereby allowing the operation team members in the operating room and the staff in the staff station to share the real-time surgery state.

The real-time surgery video may be any video insofar as it is a real-time video showing the operating room or the surgery. Examples thereof include a camera video taken by a camera installed in the operating room, showing a bird's-eye view of the operating room.

Further, in the present embodiment, the real-time surgery information includes alert information related to the surgery being conducted in the operating room. The processor 111 performs processing of displaying on the monitor 150 the real-time surgery video and alert information in association with the operating room where the surgery is conducted.

According to the present embodiment, alert information generated in the operating room can be confirmed at the staff station together with the real-time surgery video, thereby allowing the operation team members in the operating room and the staff in the staff station to share the real-time surgery state.

Further, in the present embodiment, the processor 111 stores the real-time surgery video in the storage device 112 as a past surgery video. When the processor 111 accepts an operation of reproducing a past surgery video, the processor 111 performs processing of reading out the past surgery video from the storage device 112 and displaying it on the monitor 150.

According to the present embodiment, the surgery videos can be accumulated as history information of surgery. The surgery videos can be read out and checked after the surgery. For example, the surgery videos can be used for the confirmation of surgery content, improvement of surgery, and the like.

Further, in the present embodiment, the real-time surgery information includes alert information related to the surgery being conducted in the operating room.

According to the present embodiment, alert information generated in the operating room can be confirmed at the staff station, thereby allowing the operation team members in the operating room and the staff in the staff station to share the real-time alert information.

Although FIG. 31 shows an example in which the alert information is displayed together with a real-time surgery video, the alert information may be displayed on the matrix where the surgery plan bar is shown, as explained in FIG. 19, etc.

Further, in the present embodiment, the alert information is information acquired based on the results of image analysis on the live image of the surgery being conducted in the operating room.

According to the present embodiment, an alert is automatically generated based on the results of image analysis, and the alert is shared between the operating room and the staff station.

The method for obtaining alert information based on the results of image analysis is as described in FIGS. 19 and 20, etc.

Further, in the present embodiment, the alert information is information input by an operation team member in the operating room.

According to the present embodiment, based on the state recognized by an operation team member in the operating room, the alert regarding the state can be shared between the operating room and the staff station.

The method for obtaining alert information based on the results of image analysis is as described in FIGS. 19 and 21, etc.

Figure 33:
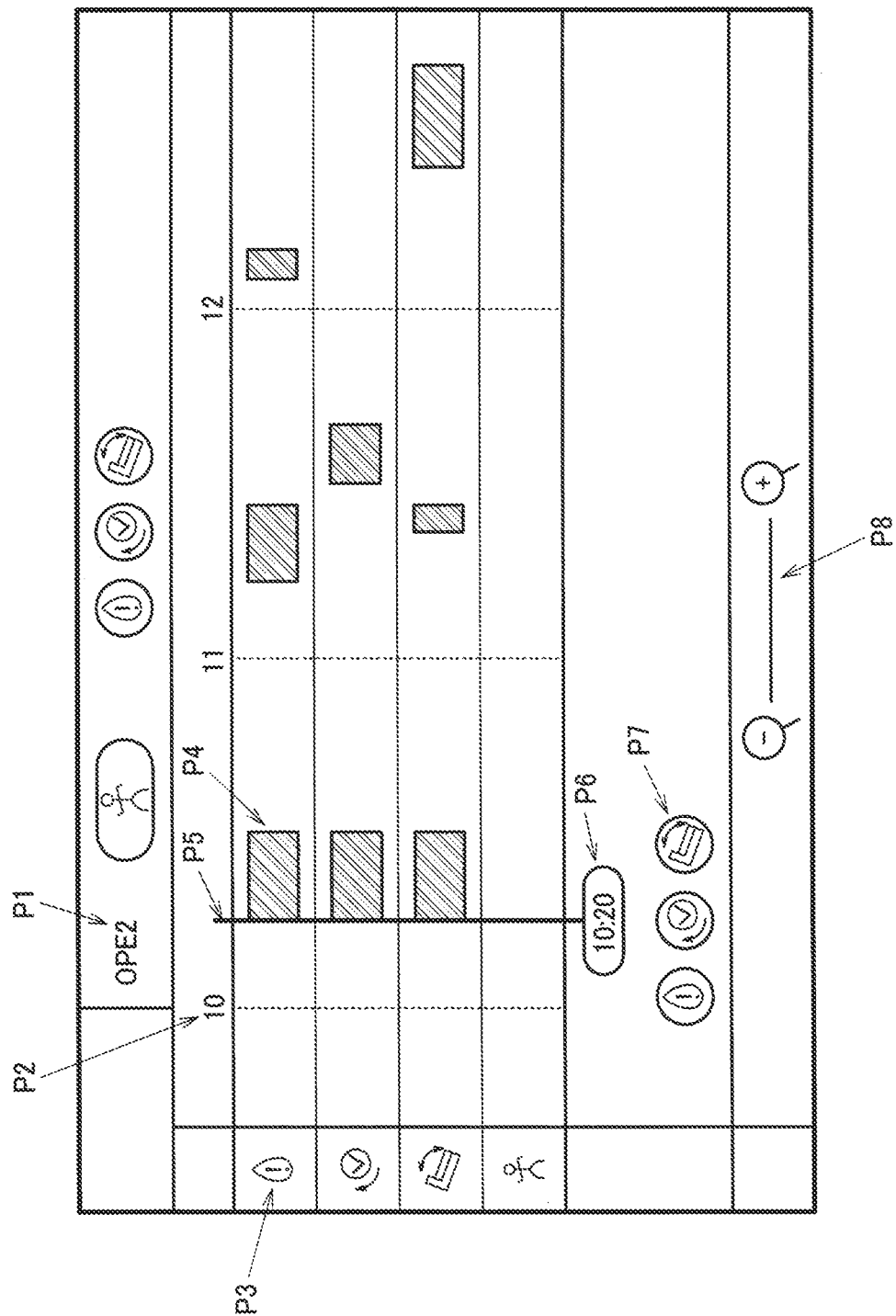
FIG. 33 is an example of timeline display screen.

FIG. 33 shows an example of a timeline display screen. The timeline display screen displays the history of alerts in the surgery. The timeline display screen can be displayed in the schedule screen during or after the surgery.

As shown in P1, the operating room number is displayed in an upper portion of the screen. As shown in P2, the horizontal axis of the timeline corresponds to the time axis. As shown in P3, the vertical axis of the timeline is an alert type axis in which alert icons are vertically arranged. The type of alert may be shown by various colors or the like instead of the icons. As shown in P4, the field of each alert displays a bar that indicates the time the alert is generated. As shown in P5, a vertical line slidable to an arbitrary time by a drag operation or the like is displayed. As shown in P6, the time at which the vertical line P5 is located is displayed under the vertical line. As shown in P7, the alerts generated at the time where the vertical line P5 is located are displayed under the time display. As shown in P8, a magnification/reduction operation bar for magnifying or reducing the timeline display is displayed.

When the processor 111 of the staff station system 100 receives information of a common alert from the operating room system 200, the processor 111 stores the information in the storage device 112. The processor 111 displays the timeline display screen on the monitor 150 based on the information of common alert stored in the storage device 112.

In the present embodiment described above, the processor 111 performs processing of displaying on the monitor 150 the timeline display screen showing the time-series alert history based on the accumulated alert information.

The present embodiment enables accumulation of the time-series alert information as the history information of the surgery, thus enabling the time-series alert information to be read out and checked after the surgery. For example, the alert information can be used for the confirmation of surgery content, improvement of surgery, and the like.

Although the embodiments to which the present disclosure is applied and the modifications thereof have been described above, the present disclosure is not limited to the embodiments and the modifications thereof, and various modifications and variations in elements may be made in implementation without departing from the spirit and scope of the present disclosure. The plurality of elements disclosed in the embodiments and the modifications described above may be combined as appropriate to form various disclosures. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A surgical support system, comprising:
a processor configured to establish communication connection with a terminal, and perform processing of displaying a display screen on the terminal to present the display screen via the terminal to a member other than a surgeon among operation team members,
wherein the display screen includes
a live image region in which a live image of surgery conducted by the operation team members is displayed, and
a supplementary region in which information regarding a supplementary operation selected by selection and input by the member via the terminal is displayed, the selection being made from a plurality of supplementary operations for management of the surgery;
the supplementary region includes
a tab region in which a plurality of tabs are arranged, different supplementary operations among the plurality of supplementary operations being allocated to the plurality of tabs, and
a work information region in which information regarding a supplementary operation allocated to a tab selected from the plurality of tabs by the selection and input is displayed;
the display screen enables setting of a first display mode in which the tab region and the work information region are displayed in the supplementary region and a second display mode in which the tab region is displayed in the supplementary region and the work information region is not displayed, and
when the second display mode is set, a display range of the supplementary region is made smaller than a display range of the supplementary region in the first display region, and a display range of the live image region is made larger than a display range of the live image region in the first display region.

2. The surgical support system as defined in claim 1,
wherein, when the terminal is a first terminal and the member is a first member, the processor establishes communication connection with the first terminal that displays information to the first member and with a second terminal that displays information to a second member among the operation team members, and performs processing of displaying the display screen on the first terminal and the second terminal,
wherein information regarding a supplementary operation selected by selection and input by the first member via the first terminal is displayed in the supplementary region of the first terminal, the selection being made from the plurality of supplementary operations, and
wherein information regarding a supplementary operation selected by selection and input by the second member via the second terminal is displayed in the supplementary region of the second terminal, the selection being made from the plurality of supplementary operations.

3. The surgical support system as defined in claim 1, wherein the display screen includes a common alert region in which a common alert regarding at least one supplementary operation out of the plurality of supplementary operations is displayed outside the supplementary region, regardless of which one of the plurality of supplementary operations is selected by the selection and input.

4. The surgical support system as defined in claim 1, wherein the plurality of tabs include
first to n-th (n being an integer of 2 or more) tabs to which first to n-th supplementary operations are allocated, and
a fixed display tab in which one or more supplementary operations out of the first to n-th supplementary operations are set as supplementary operations that are fixedly displayed, and
wherein
when one of the first to n-th tabs is selected by the selection and input, the work information region displays information regarding a supplementary operation allocated to the selected tab, and
when the fixed display tab is selected by the selection and input, the work information region displays information regarding the supplementary operations that are fixedly displayed.

5. The surgical support system as defined in claim 1, wherein
when the terminal is a first terminal and the member is a first member, the processor establishes communication connection with the first terminal that displays information to the first member and with a second terminal that displays information to a second member among the operation team members, and performs processing of displaying
the display screen on the first terminal and the second terminal, the display screen of the first terminal displays a display mode out of the first display mode and the second display mode set in accordance with setting input from the first member via the first terminal, and
the display screen of the second terminal displays a display mode out of the first display mode and the second display mode set in accordance with setting input from the second member via the second terminal.

6. A surgical support system, comprising:
a processor configured to establish communication connection with a terminal, and perform processing of displaying a display screen on the terminal to present the display screen via the terminal to a member other than a surgeon among operation team members,
wherein the display screen includes
a live image region in which a live image of surgery conducted by the operation team members is displayed, and
a supplementary region in which information regarding a supplementary operation selected by selection and input by the member via the terminal is displayed, the selection being made from a plurality of supplementary operations for management of the surgery;
when the terminal is a first terminal and the member is a first member, the processor establishes communication connection with the first terminal that displays information to the first member and with a second terminal that displays information to a second member among the operation team members, and performs processing of displaying the display screen on the first terminal and the second terminal,
information regarding a supplementary operation selected by selection and input by the first member via the first terminal is displayed in the supplementary region of the first terminal, the selection being made from the plurality of supplementary operations,
information regarding a supplementary operation selected by selection and input by the second member via the second terminal is displayed in the supplementary region of the second terminal, the selection being made from the plurality of supplementary operations;

the processor accepts a first input value input from the first member to the supplementary region of the first terminal and a second input value input from the second member to the supplementary region of the second terminal with regard to a specific supplementary operation out of the plurality of supplementary operations, and when the first input value and the second input value are different, the processor performs processing of displaying an alert sign indicating the difference in the display screens of the first terminal and the second terminal.

7. The surgical support system as defined in claim 6, wherein the specific supplementary operation is at least one of an operation of counting the number of articles inserted into the body of a patient or an operation of counting the number of the articles collected from the body of the patient, and the first input value and the second input value are count values in the counting operations.

8. The surgical support system as defined in claim 6, wherein the supplementary region includes a tab region in which a plurality of tabs are arranged, different supplementary operations among the plurality of supplementary operations being allocated to the plurality of tabs, a work information region in which information regarding a supplementary operation allocated to a tab selected from the plurality of tabs by the selection and input is displayed, and wherein the alert sign is displayed on a tab corresponding to the specific supplementary operation out of the plurality of tabs.

9. The surgical support system as defined in claim 1, wherein the live image displayed on a monitor of the surgeon is displayed in the live image region.

10. The surgical support system as defined in claim 3, wherein the processor establishes communication connection with a staff station terminal positioned in the staff station outside an operating room where the surgeon performs surgery, and transmits information of the common alert to the staff station terminal to display an alert synchronized with the common alert on a monitor of the staff station terminal.

11. The surgical support system as defined in claim 10, wherein, when a predetermined surgery situation is detected based on a result of image analysis on the live image, the processor transmits information of the common alert regarding the predetermined surgery situation to the staff station terminal.

12. The surgical support system as defined in claim 10, wherein, when accepting an instruction input from the member via the terminal, the processor transmits information of the common alert regarding the instruction input to the staff station terminal.

13. The surgical support system as defined in claim 10, wherein the processor transmits information of the common alert to the staff station terminal in association with surgery performed by the surgeon to display the alert synchronized with the common alert on a monitor of the staff station terminal in association with the surgery performed by the surgeon among the plurality of surgeries managed by the staff station terminal.

14. A surgical support system, comprising:

a processor configured to establish communication connection with a terminal, and perform processing of displaying a display screen on the terminal to present the display screen via the terminal to a member other than a surgeon among operation team members, wherein the display screen includes a live image region in which a live image of surgery conducted by the operation team members is displayed, and a supplementary region in which information regarding a supplementary operation selected by selection and input by the member via the terminal is displayed, the selection being made from a plurality of supplementary operations for management of the surgery;

wherein the display screen includes a common alert region in which a common alert regarding at least one supplementary operation out of the plurality of supplementary operations is displayed outside the supplementary region, regardless of which one of the plurality of supplementary operations is selected by the selection and input;

wherein the processor establishes communication connection with a staff station terminal positioned in the staff station outside an operating room where the surgeon performs surgery, transmits information of the common alert to the staff station terminal to display an alert synchronized with the common alert on a monitor of the staff station terminal receives a scheduled end time of the surgery from the staff station terminal that manages schedule of surgery performed by the surgeon, performs processing of displaying the received scheduled end time in the display screen, and when the scheduled end time is rescheduled in the staff station terminal, performs processing of displaying the rescheduled scheduled end time in the display screen.

15. The surgical support system as defined in claim 1, which comprises the terminal.

16. The surgical support system as defined in claim 6, wherein the display screen includes a common alert region in which a common alert regarding at least one supplementary operation out of the plurality of supplementary operations is displayed outside the supplementary region, regardless of which one of the plurality of supplementary operations is selected by the selection and input.

17. The surgical support system as defined in claim 6, wherein the supplementary region includes a tab region in which a plurality of tabs are arranged, different supplementary operations among the plurality of supplementary operations being allocated to the plurality of tabs, and a work information region in which information regarding a supplementary operation allocated to a tab selected from the plurality of tabs by the selection and input is displayed.

18. The surgical support system as defined in claim 6, wherein the plurality of tabs include first to n-th (n being an integer of 2 or more) tabs to which first to n-th supplementary operations are allocated, and a fixed display tab in which one or more supplementary operations out of the first to n-th supplementary operations are set as supplementary operations that are fixedly displayed, and wherein when one of the first to n-th tabs is selected by the selection and input, the work information region displays information regarding a supplementary operation allocated to the selected tab, and when the fixed display tab is selected by the selection and input, the work information region displays information regarding the supplementary operations that are fixedly displayed.

19. The surgical support system as defined in claim 14, wherein, when the terminal is a first terminal and the member is a first member, the processor establishes communication connection with the first terminal that displays information to the first member and with a second terminal that displays information to a second member among the operation team members, and performs processing of displaying the display screen on the first terminal and the second terminal, wherein information regarding a supplementary operation selected by selection and input by the first member via the first terminal is displayed in the supplementary region of the first terminal, the selection being made from the plurality of supplementary operations, and wherein information regarding a supplementary operation selected by selection and input by the second member via the second terminal is displayed in the supplementary region of the second terminal, the selection being made from the plurality of supplementary operations.

20. The surgical support system as defined in claim 14, wherein the supplementary region includes a tab region in which a plurality of tabs are arranged, different supplementary operations among the plurality of supplementary operations being allocated to the plurality of tabs, and a work information region in which information regarding a supplementary operation allocated to a tab selected from the plurality of tabs by the selection and input is displayed.

\* \* \* \* \*